US007169908B2

(12) United States Patent
Lester et al.

(10) Patent No.: US 7,169,908 B2
(45) Date of Patent: Jan. 30, 2007

(54) PURIFICATION OF POLYPEPTIDES

(75) Inventors: Philip M. Lester, San Lorenzo, CA (US); Josefine Persson, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 117 days.

(21) Appl. No.: 10/754,212

(22) Filed: Jan. 8, 2004

(65) Prior Publication Data
US 2005/0037456 A1 Feb. 17, 2005

Related U.S. Application Data

(60) Provisional application No. 60/439,418, filed on Jan. 9, 2003.

(51) Int. Cl.
C07K 1/02 (2006.01)
C12P 21/02 (2006.01)
(52) U.S. Cl. .............. 530/412; 530/419; 435/69.1; 435/69.6
(58) Field of Classification Search ............ 435/326, 435/69.6, 69.1; 546/102; 424/141.1, 176.1; 514/12; 530/412, 419
See application file for complete search history.

(56) References Cited

U.S. PATENT DOCUMENTS

| 3,607,857 A * | 9/1971 | Nelson ............... 530/389.6 |
| 3,930,953 A | 1/1976 | Stark |
| 4,563,303 A * | 1/1986 | Ginnaga et al. .......... 530/396 |
| 5,440,028 A * | 8/1995 | Buchholz et al. ......... 536/124 |
| 5,641,870 A | 6/1997 | Rinderknecht et al. |
| 5,665,866 A | 9/1997 | Weir et al. |
| 5,714,583 A | 2/1998 | Foster et al. |
| 5,760,189 A | 6/1998 | Vicik et al. |
| 6,121,428 A | 9/2000 | Blank et al. |
| 6,214,984 B1 | 4/2001 | Zapata |
| 6,322,997 B1 | 11/2001 | Blank et al. |
| 2002/0146406 A1* | 10/2002 | Mayo .................. 424/94.63 |

FOREIGN PATENT DOCUMENTS

| DE | 3604947 | 8/1987 |
| EP | 0 226 639 | 7/1987 |
| EP | 0 227 833 | 7/1987 |

(Continued)

OTHER PUBLICATIONS

Azegami et al., "Induction of bacteriolytic enzyme from pyocinogenic *Pseudomonas aeruginosa* and its enzymatic properties," Microbios 23:73-81, 1978.*

(Continued)

*Primary Examiner*—Jon Weber
*Assistant Examiner*—Rosanne Kosson
(74) *Attorney, Agent, or Firm*—Janet E. Hasak

(57) ABSTRACT

A method for purifying a desired heterologous polypeptide from microbial fermentation broth or homogenate in which it is produced and solubilized is described. This method involves adding to the broth or homogenate an effective amount of a solution of 6,9-diamino-2-ethoxyacridine lactate (ethacridine lactate) to precipitate host cell impurities under conditions wherein the majority of polypeptide remains soluble, and separating the desired polypeptide from the broth or homogenate. The broth or homogenate containing the ethacridine lactate and polypeptide is also disclosed.

30 Claims, 13 Drawing Sheets

FOREIGN PATENT DOCUMENTS

| EP | 0 250 288 | | 12/1987 |
|---|---|---|---|
| EP | 0 418 647 | | 3/1991 |
| JP | 60-258127 | | 12/1985 |
| JP | 11341947 A | * | 12/1999 |
| SU | 944580 | | 7/1982 |

OTHER PUBLICATIONS

Plückthun, "*Escherichia coli* producing recombinant antibodies," Bioprocess Technology, Recombinant Microbes for Industrial and Agricultural Applications, Marcel Dekker, New York, 1994, chap. 13, pp. 233-252.*

Aizenman et al., "Salvin, an antibiotic from Salvia officinalis" *Mikrobiol—Zh.* (English Equivalent Attached) 44:69-72 (1982).

Aristidou et al., "Effects of Glycine Supplement on Protein Production and Release in Recombinant *Escherichia coli*" *Biotechnology Letters* 15:331-336 (1993).

Cohn et al., "A System for the Separation of the Components of Human Blood: Quantitative Procedures for the Separation of the Protein Components of Human Plasma" *J. Amer. Chem. Soc.* 72:465-474 (1950).

Cumming et al., "Flocculation of *Esch. coli* cationic polymers: A model for the dose curve based on charge" *Bioseparation* 6:17-23 (1996).

Englard and Seifter, "[22] Precipitation Techniques" *Methods in Enzymology* 182:285-300 (1990).

Engler, C., "Cell Breakage" *Protein Purification Process Engineering* pp. 37-55 (1994).

Franek and Dolnikova, "Monoclonal Antibody Technology: Striving for Lower Cost and Higher Biological Safety" *Biotech-Forum-Eur* 7:468-470 (1990).

Franek, F., "Purification of IgG Monoclonal Antibodies from Ascitic Fluid Based on Rivanol Precipitation" *Methods in Enzymology*, Langone JJ, Van Vunakis H vol. 121:631-638 (1986).

Horejsi and Smetana, "The Isolation of Gamma Globulin from Blood-Serum by Rivanol" *Acta Med. Scand.* 155:65-70 (1956).

Jendrisak, J., "The use of polyethyleneimine in protein purification" *Protein purification: micro to macro*, Alan R. Liss, Inc. pp. 75-97 (1987).

Kelley, B. and Hatton, A, "The fermentation/ downstream processing interface" *Bioseparation* 1:333-349 (1991).

Kipriyanov and Little., "Generation of Recombinant Antibodies." *Mol. Biotech.* 12:173-201 (1999).

Lutsik and Antoniuk, "New fucose-specific lectin from the bark of dwarf almond golden rain Laburnum anagyroides Medik: purification, properties and immunochemical specificity" *Biokhimiya* (English Equivalent Attached) 47:1710-1715 (1982).

Miller, K., "Biochemistry: Rivanol, Resin and the Isolation of Thrombins" *Nature* 184:450 (1959).

Moir and Mao, "Protein Secretion Systems in Microbial and Mammalian Cells" *Bioprocess. Technol.* 9:67-94 (1990).

Neurath and Brunner, "Fractionation of Proteins with Different Isoelectric Points by Rivanol" *Experientia* 25:668-671 (1969).

Niederauer and Glatz, "Selective Precipitation" *Advances in Biochemical Engineering Biotechnology*, Spreinger-Verlag, Berlin Heidelberg vol. 47:160-188 (1992).

Rothwell et al., "Radiometric Assay for Direct Quantitation of Rat Liver Cytochrome P-450b Using Monoclonal Antibodies" *Analytical Biochemistry* 149:197-201 (1985).

Salt et al., "Selective flocculation of cellular contaminants from soluble proteins using polyethyleneimine: A study of several organisms and polymer molecular weights" *Enzyme and Microbial Technology* 17:107-113 (1995).

Sassenfeld, "Engineering proteins for purification" *TIBTECH* 8:88-93 (1990).

Scawen and Melling, "Large-scale extraction and purification of enzymes and other proteins" *Handbook of Enzyme Biotechnology*, 2nd edition, Chapter 2, pp. 15-53 (1985).

Scopes *Protein Purification Principles and Practice*, 3rd edition p. 171 (1994).

Scopes, R. *Protein Purification Principles and Practice*, 2nd edition pp. 21-71 (1987).

Skerra and Pluckthun, "Assembly of a functional immunoglobulin $F_v$ fragment in *Escherichia coli*" *Science* 240:1038-1041 (1988).

Spears, "Overview of Downstream Processing" *Biotechnology*, Rehm vol. 3—Bioprocessing:40-51 (1993).

Steinbuch and Niewiarowski, "Rivanol in the Preparation of Plasminogen (Profibrinolysin)" *Nature* 186:87-88 (1960).

Sternberg and Hershberger, "Separation of Proteins with Polyacrylic Acids" *Biochem et Biophys. Acta* 342:195-206 (1974).

Strandberg et al., "Large-Scale Fermentation and Purification of a Recombinant Protein from *Escherichia coli*" *Process Biochemistry* 26:225-234 (1991).

Tchernov et al., "Purification of phycobiliproteins from *Nostoc* sp. by aminohexyl-Sepharose chromatography" *J. Biotechnol.* 69:69-73 (1999).

Wang et al., "Enzyme Isolation" *Fermentation and Enzyme Technology* pp. 253-256 (1979).

Wheelwright, "Precipitation and Extraction" *Protein Purification: Design and Scale up of Downstream Processing*, Chapter 8, pp. 87-98 (1991).

Windholtz et al. *The Merck Index*, 10th edition pp. 300, 1364 (1983).

Audran et al., "Obtention d'une preparation d'immunoglobulines G,A,M (IgGAM) a usage therapeutique" *Revue Francaise de Transfusion et Immuno-Hematologie* 18:119-135 (1975).

Azegami et al., "Induction of bacteriolytic enzyme from pyocinogenic *Pseudomonas aeruginosa* and its enzymatic properties" *Microbios* 23:73-81 (1978).

Database WPI, "Section Ch, Week 197119" *XP002294542*, Derwent Publications Ltd. (Oct. 19, 1970).

Database WPI, "Section Ch, Week 197541" *XP002294543*, Derwent Publications Ltd. (Jun. 12, 1975).

Database WPI, "Section Ch, Week 198606" *XP002294562*, Derwent Publications Ltd. (Dec. 20, 1985).

Fahrner et al., "Industrial Purification of Pharmaceutical Antibodies: Development, Operation, and Validation of Chromatography Processes" *Biotechnology & Genetic Engineering Reviews* 18:301-327 (2001).

Flamez et al., "Production in *Escherichia coli* of a functional murine and murine: :human chimeric F(ab')2 fragment and mature antibody directed against human placental alkaline phosphatase" *J. Biotechnology* 42:133-143 (1995).

Page, M. & Thorpe, R., "IgG Purification" *Methods in Molecular Biology* 80:95-111 (1998).

Persson, J. & Lester, P., "Purification of Antibody and Antibody-Fragment From *E. coli* Homogenate Using 6, 9-Diamino-2-ethoxyacridine Lactate as Precipitation Agent" *Biotechnology and Bioengineering* 87:424-434 (2004).

Pluckthun, Andreas, "*Escherichia coli* Producing Recombinant Antibodies" *Bioprocess Technology* pp. 233-252 (1994).

Raffai et al., "Bacterial Expression and Purification of the Fab Fragment of a Monoclonal Antibody Specific for the Low-Density Lipoprotein Receptor-Binding Site of Human Apolipoprotein E" *Protein Expression and Purification* 16:84-90 (1999).

Tsugita and Inouye, "Purification of bacteriophage T4 lysozyme" *Journal of Biological Chemistry* 243 (2) :391-397 (Jan. 25, 1968).

* cited by examiner

Figure 1: Schematic of the anti-CD18 Fab'2 (-leucine zipper) Plasmids
pS1130
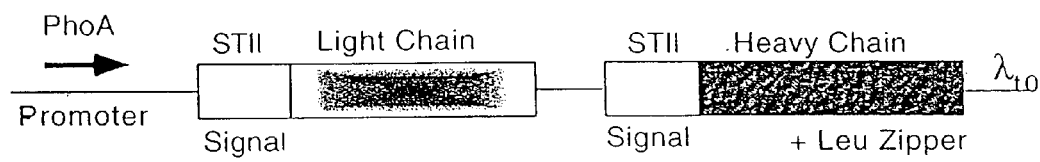
pxCD18-7T3
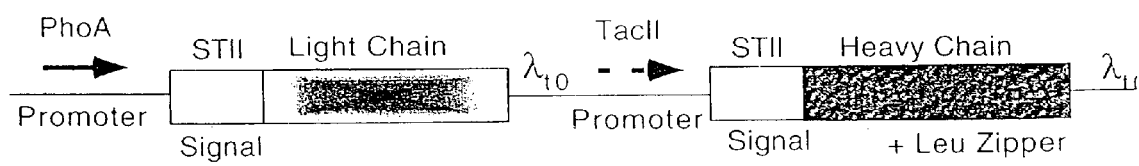

Figure 2
Anti-CD18-7T3.DNA

```
GAATTCAACTTCTCCATACTTTGGATAAGGAAATACAGACATGAAAAATCTCATTGCTGA
GTTGTTATTTAAGCTTGCCCAAAAAGAAGAAGAGTCGAATGAACTGTGTGCGCAGGTAGA
AGCTTTGGAGATTATCGTCACTGCAATGCTTCGCAATATGGCGCAAAATGACCAACAGCG
GTTGATTGATCAGGTAGAGGGGGCGCTGTACGAGGTAAAGCCCGATGCCAGCATTCCTGA
CGACGATACGGAGCTGCTGCGCGATTACGTAAAGAAGTTATTGAAGCATCCTCGTCAGTA
AAAAGTTAATCTTTTCAACAGCTGTCATAAAGTTGTCACGGCCGAGACTTATAGTCGCTT
TGTTTTTATTTTTTAATGTATTTGTAACTAGTACGCAAGTTCACGTAAAAAGGGTATCTA
GAATTATGAAAAGAATATCGCATTTCTTCTTGCATCTATGTTCGTTTTTTCTATTGCTA
CAAACGCGTACGCTGATATCCAGATGACCCAGTCCCCGAGCTCCCTGTCCGCCTCTGTGG
GCGATAGGGTCACCATCACCTGTCGTGCCAGTCAGGACATCAACAATTATCTGAACTGGT
ATCAACAGAAACCAGGAAAAGCTCCGAAACTACTGATTTACTATACCTCCACCCTCCACT
CTGGAGTCCCTTCTCGCTTCTCTGGTTCTGGTTCTGGGACGGATTACACTCTGACCATCA
GCAGTCTGCAACCGGAGGACTTCGCAACTTATTACTGTCAGCAAGGTAATACTCTGCCGC
CGACGTTCGGACAGGGCACGAAGGTGGAGATCAAACGAACTGTGGCTGCACCATCTGTCT
TCATCTTCCCGCCATCTGATGAGCAGTTGAAATCTGGAACTGCCTCTGTTGTGTGCCTGC
TGAATAACTTCTATCCCAGAGAGGCCAAAGTACAGTGGAAGGTGGATAACGCCCTCCAAT
CGGGTAACTCCCAGGAGAGTGTCACAGAGCAGGACAGCAAGGACAGCACCTACAGCCTCA
GCAGCACCCTGACGCTGAGCAAAGCAGACTACGAGAAACACAAAGTCTACGCCTGCGAAG
TCACCCATCAGGGCCTGAGCTCGCCCGTCACAAAGAGCTTCAACAGGGGAGAGTGTTAAT
TAAATCCTCTACGCCGGACGCATCGTGGCGAGCTCGGTACCCGGGGATCTAGGCCTAACG
CTCGGTTGCCGCCGGGCGTTTTTTATTGTTGCCGACGCGCATCTCGACTGCACGGTGCAC
CAATGCTTCTGGCGTCAGGCAGCCATCGGAAGCTGTGGTATGGCTGTGCAGGTCGTAAAT
CACTGCATAATTCGTGTCGCTCAAGGCGCACTCCCGTTCTGGATAATGTTTTTTGCGCCG
ACATCATAACGGTTCTGGCAAATATTCTGAAATGAGCTGTTGACAATTAATCATCGAACT
AGTTTAATGTGTGGAATTGTGAGCGGATAACAATTAAGCTTAGGATCTAGAATTATGAAG
AAGAATATTGCGTTCCTACTTGCCTCTATGTTTGTCTTTTCTATAGCTACAAACGCGTAC
GCTGAGGTTCAGCTGGTGGAGTCTGGCGGTGGCCTGGTGCAGCCAGGGGGCTCACTCCGT
TTGTCCTGTGCAACTTCTGGCTACACCTTTACCGAATACACTATGCACTGGATGCGTCAG
GCCCCGGGTAAGGGCCTGGAATGGGTTGCAGGGATTAATCCTAAAAACGGTGGTACCAGC
CACAACCAGAGGTTCATGGACCGTTTCACTATAAGCGTAGATAAATCCACCAGTACAGCC
TACATGCAAATGAACAGCCTGCGTGCTGAGGACACTGCCGTCTATTATTGTGCTAGATGG
CGAGGCCTGAACTACGGCTTTGACGTCCGTTATTTTGACGTCTGGGGTCAAGGAACCCTG
GTCACCGTCTCCTCGGCCTCCACCAAGGGCCCATCGGTCTTCCCCCTGGCACCCTCCTCC
AAGAGCACCTCTGGGGGCACAGCGGCCCTGGGCTGCCTGGTCAAGGACTACTTCCCCGAA
CCGGTGACGGTGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCCCTCCAGCAGC
TTGGGCACCCAGACCTACATCTGCAACGTGAATCACAAGCCCAGCAACACCAAGGTCGAC
AAGAAAGTTGAGCCCAAATCTTGTGACAAAACTCACACATGCCCGCCGTGCCCAGCACCA
GAACTGCTGGGCGGCCGCATGAAACAGCTAGAGGACAAGGTCGAAGAGCTACTCTCCAAG
AACTACCACCTAGAGAATGAAGTGGCAAGACTCAAAAAGCTTGTCGGGGAGCGCTAAGCA
TGCGACGGCCCTAGAGTCCCTAACGCTCGGTTGCCGCCGGGCGTTTTTTATTGTTAACTC
ATGTTTGACAGCTTATCATCGATAAGCTTTAATGCGGTAGTTTATCACAGTTAAATTGCT
AACGCAGTCAGGCACCGTGTATGAAATCTAACAATGCGCTCATCGTCATCCTCGGCACCG
TCACCCTGGATGCTGTAGGCATAGGCTTGGTTATGCCGGTACTGCCGGGCCTCTTGCGGG
ATATCGTCCATTCCGACAGCATCGCCAGTCACTATGGCGTGCTGCTAGCGCTATATGCGT
```

(SEQ ID NO:1)

Figure 3
Anti-CD18-7T3.Protein

FIG. 3A: STII + Anti-CD18 light chain

MKKNIAFLLASMFVFSIATNAYADIQMTQSPSSLSASVGDRVTITCRASQDINNYLNWY
QQKPGKAPKLLIYYTSTLHSGVPSRFSGSGSGTDYTLTISSLQPEDFATYYCQQGNTLP
PTFGQGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGE
C (SEQ ID NO:2)

FIG. 3B: STII + Anti-CD18 heavy chain

MKKNIAFLLASMFVFSIATNAYAEVQLVESGGGLVQPGGSLRLSCATSGYTFTEYTMHW
MRQAPGKGLEWVAGINPKNGGTSHNQRFMDRFTISVDKSTSTAYMQMNSLRAEDTAVYY
CARWRGLNYGFDVRYFDVWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKP
SNTKVDKKVEPKSCDKTHTCPPCPAPELLGGRMKQLEDKVEELLSKNYHLENEVARLKK
LVGER (SEQ ID NO:3)

Figure 4: Schematic of the anti-Tissue Factor IgG1 Plasmids
paTF130
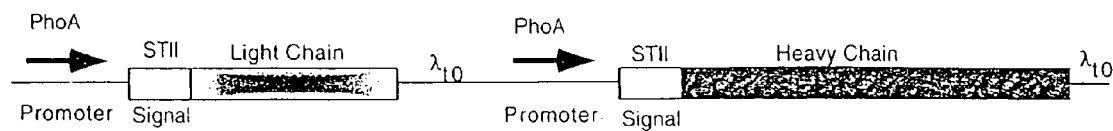
pxTF-7T3FL
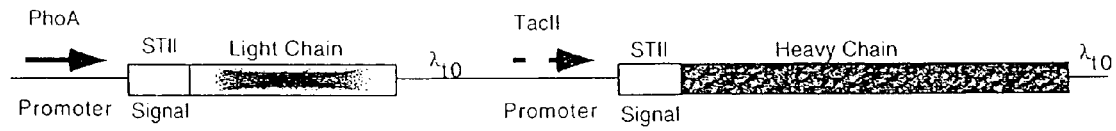

Figure 5
Anti-TF-7T3FL.DNA

```
GAATTCAACTTCTCCATACTTTGGATAAGGAAATACAGACATGAAAAATCTCATTGCTGA
GTTGTTATTTAAGCTTGCCCAAAAAGAAGAAGAGTCGAATGAACTGTGTGCGCAGGTAGA
AGCTTTGGAGATTATCGTCACTGCAATGCTTCGCAATATGGCGCAAAATGACCAACAGCG
GTTGATTGATCAGGTAGAGGGGGCGCTGTACGAGGTAAAGCCCGATGCCAGCATTCCTGA
CGACGATACGGAGCTGCTGCGCGATTACGTAAAGAAGTTATTGAAGCATCCTCGTCAGTA
AAAAGTTAATCTTTTCAACAGCTGTCATAAAGTTGTCACGGCCGAGACTTATAGTCGCTT
TGTTTTTATTTTTAATGTATTTGTAACTAGTACGCAAGTTCACGTAAAAAGGGTATCTA
GAATTATGAAAAAGAATATCGCATTTCTTCTTGCATCTATGTTCGTTTTTTCTATTGCTA
CAAACGCGTACGCTGATATCCAGATGACCCAGTCCCCGAGCTCCCTGTCCGCCTCTGTGG
GCGATAGGGTCACCATCACCTGCAGAGCCAGTCGCGACATCAAGAGCTATCTGAACTGGT
ATCAACAGAAACCAGGAAAAGCTCCGAAAGTACTGATTTACTATGCTACTAGTCTCGCTG
AAGGAGTCCCTTCTCGCTTCTCTGGATCCGGTTCTGGGACGGATTACACTCTGACCATCA
GCAGTCTGCAGCCAGAAGACTTCGCAACTTATTACTGTCTTCAGCACGGAGAGTCTCCAT
GGACATTTGGACAGGGTACCAAGGTGGAGATCAAACGAACTGTGGCTGCACCATCTGTCT
TCATCTTCCCGCCATCTGATGAGCAGTTGAAATCTGGAACTGCTTCTGTTGTGTGCCTGC
TGAATAACTTCTATCCCAGAGAGGCCAAAGTACAGTGGAAGGTGGATAACGCCCTCCAAT
CGGGTAACTCCCAGGAGAGTGTCACAGAGCAGGACAGCAAGGACAGCACCTACAGCCTCA
GCAGCACCCTGACGCTGAGCAAAGCAGACTACGAGAAACACAAAGTCTACGCCTGCGAAG
TCACCCATCAGGGCCTGAGCTCGCCCGTCACAAAGAGCTTCAACAGGGGAGAGTGTTAAT
TAAATCCTCTACGCCGGACGCATCGTGGCGAGCTCGGTACCCGGGGATCTAGGCCTAACG
CTCGGTTGCCGCCGGGCGTTTTTTATTGTTGCCGACGCGCATCTCGACTGCACGGTGCAC
CAATGCTTCTGGCGTCAGGCAGCCATCGGAAGCTGTGGTATGGCTGTGCAGGTCGTAAAT
CACTGCATAATTCGTGTCGCTCAAGGCGCACTCCCGTTCTGGATAATGTTTTTGCGCCG
ACATCATAACGGTTCTGGCAAATATTCTGAAATGAGCTGTTGACAATTAATCATCGAACT
AGTTTAATGTGTGGAATTGTGAGCGGATAACAATTAAGCTTAGGATCTAGAATTATGAAG
AAGAATATTGCGTTCCTACTTGCCTCTATGTTTGTCTTTTCTATAGCTACAAACGCGTAC
GCTGAGGTTCAGCTGGTGGAGTCTGGCGGTGGCCTGGTGCAGCCAGGGGGCTCACTCCGT
TTGTCCTGTGCAGCTTCTGGCTTCAATATTAAGGAGTACTACATGCACTGGGTCCGTCAG
GCCCCGGGTAAGGGCCTGGAATGGGTTGGATTGATTGATCCAGAGCAAGGCAACACGATC
TATGACCCGAAGTTCCAGGACCGTGCCACTATAAGCGCTGACAATTCCAAAAACACAGCA
TACCTGCAGATGAACAGCCTGCGTGCTGAGGACACTGCCGTCTATTATTGTGCTCGAGAC
ACGGCCGCTTACTTCGACTACTGGGGTCAAGGAACCCTGGTCACCGTCTCCTCGGCCTCC
ACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTC
TACTCCCTCAGCAGCGTGGTGACTGTGCCCTCTAGCAGCTTGGGCACCCAGACCTACATC
TGCAACGTGAATCACAAGCCCAGCAACACCAAGGTGGACAAGAAAGTTGAGCCCAAATCT
TGTGACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACTGGTACGTG
GACGGCGTGGAGGTGCATAATGCCAAGACAAAGCCGCGGGAGGAGCAGTACAACAGCACG
TACCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGAAGAGATGACC
AAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGAAG
AGCCTCTCCCTGTCTCCGGGTAAATAAGCATGCGACGGCCCTAGAGTCCCTAACGCTCGG
TTGCCGCCGGGCGTTTTTTATTGTTAACTCATGTTTGACAGCTTATCATCGATAAGCTTT
AATGCGGTAGTTTATCACAGTTAAATTGCTAACGCAGTCAGGCACCGTGTATGAAATCTA
ACAATGCGCTCATCGTCATCCTCGGCACCGTCACCCTGGA
```

(SEQ ID NO:4)

Figure 6
Anti-TF-7T3FL.Protein

FIG. 6A: STII + Anti-TF light chain

MKKNIAFLLASMFVFSIATNAYADIQMTQSPSSLSASVGDRVTITCRASRDIKSYLNWY
QQKPGKAPKVLIYYATSLAEGVPSRFSGSGSGTDYTLTISSLQPEDFATYYCLQHGESP
WTFGQGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGE
C (SEQ ID NO:5)

FIG. 6B: STII + Anti-TF heavy chain

MKKNIAFLLASMFVFSIATNAYAEVQLVESGGGLVQPGGSLRLSCAASGFNIKEYYMHW
VRQAPGKGLEWVGLIDPEQGNTIYDPKFQDRATISADNSKNTAYLQMNSLRAEDTAVYY
CARDTAAYFDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK (SEQ ID NO:6)

anti-CD18 F(ab')₂ anti-TF F(ab')₂ anti-TF (Ab)

Fig. 10A Water

Fig. 10B Ethacridine lactate

Fig. 11

PURIFICATION OF POLYPEPTIDES

RELATED APPLICATIONS

This application is a non-provisional application filed under 37 CFR 1.53(b)(1), claiming priority under 35 USC 119(e) to provisional application No. 60/439,418 filed Jan. 9, 2003, the contents of which are incorporated herein by reference.

BACKGROUND OF THE INVENTION

1. Field of the Invention

This invention relates to a process for purifying polypeptides of interest from microbial fermentation broth or homogenate. More particularly, a precipitation agent is introduced to the broth or homogenate to effect, for example, protein, DNA, and cell debris removal.

2. Description of Related Art

The advent of recombinant technology now allows for the production of high levels of proteins within suitably transformed host cells. As a result, there is increased demand for fast, robust, and efficient purification methods to recover the recombinantly produced proteins. Generally, proteins are produced by culturing cells, such as mammalian, insect, fungal, and bacterial cell lines, engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins can be secreted directly from the cell into the surrounding growth media; others are made intracellularly. For polypeptides produced in mammalian cells, the purification scheme is significantly easier than for polypeptides produced in other types of host cells. Mammalian cells export the polypeptides so that they can be collected from the growth media, where they are present in relatively pure form. However, if the polypeptide is produced in a non-mammalian cell, e.g., a microorganism such as fungi or *E. coli*, the polypeptide will be recovered inside the cell or in the periplasmic space (Kipriyanov and Little, *Molecular Biotechnology*, 12: 173–201 (1999); Skerra and Pluckthun, *Science*, 240: 1038–1040 (1988)). Hence, it is necessary to release the protein from the cells to the extracellular medium by extraction such as cell lysis. Such disruption releases the entire contents of the cell into the homogenate, and in addition produces subcellular fragments that are difficult to remove due to their small size. These are generally removed by differential centrifugation or by filtration.

Cell lysis is typically accomplished using mechanical disruption techniques such as homogenization or head milling. While the protein of interest is generally effectively liberated, such techniques have several disadvantages (Engler, *Protein Purification Process Engineering*, Harrison eds., 37–55 (1994)). Temperature increases, which often occur during processing, may result in inactivation of the protein. Moreover, the resulting suspension contains a broad spectrum of contaminating proteins, nucleic acids, and polysaccharides. Nucleic acids and polysaccharides increase solution viscosity, potentially complicating subsequent processing by centrifugation, cross-flow filtration, or chromatography. Complex associations of these contaminants with the protein of interest can complicate the purification process and result in unacceptably low yields.

As such, more selective means of releasing intracellular proteins facilitates further downstream processing. Several techniques have been reported to permeabilize cells and/or to extract intracellular proteins. These methods include the use of solvents, detergents, chaotropic agents, antibiotics, enzymes, and chelating agents to enhance cell permeability and/or promote extraction. Additions of certain compounds, such as glycine, to the fermentation medium during culture growth have also been reported to promote release of certain intracellular enzymes. Finally, techniques such as freeze-thaw treatment or osmotic shock have also been shown to release subsets of intracellular proteins.

However, these techniques are not necessarily applicable to all intracellular microbial proteins, and all have limited application for large-scale processing, and/or other disadvantages. For example, while solvents such as toluene and chloroform promote release of intracellular proteins, these substances are known to be toxic and/or carcinogenic (Windholtz et al., *The Merck Index* 10th Edition: 300 and 1364 (1983)). Ionic detergents, such as SDS, often irreversibly denature isolated proteins. Although non-ionic detergents are not normally denaturing, the recovered proteins are often associated with detergent micelles that can require additional processing to yield detergent-free protein. Chaotropic agents, such as urea and guanidine hydrochloride, can be denaturing at the concentrations required for complete release, and their effectiveness may be dependent on the growth phase of the culture. The use of lysozyme, which provides for a relatively gentle means of protein release, is limited because of its relatively high cost and because of the subsequent need to purify the protein of interest from the enzyme reagent. In addition, chelating agents, often used to enhance the effectiveness of other permeabilizing/release techniques such as lysozyme or toluene extraction, suffer from the disadvantage of non-specific release of host proteins.

Other methods for protein release also have disadvantages. For example, osmotic shock, in which cells are suspended in a high osmolarity medium, recovered, and subsequently placed in a low osmolarity buffer, requires additional processing steps with respect to other extraction alternatives (Moir et al., *Bioprocess Technology*, Asenjo eds: 67–94 (990)) or necessitates the handling of large liquid volumes at low temperatures. This renders the method unattractive for large-scale processing.

Freeze-thaw treatment also releases intracellular proteins, although relatively low yields often result in multiple cycles or additional processing requirements. In addition, cell paste freezing is an added non-trivial processing requirement compared with other extraction alternatives.

Finally, reagents, such as glycine, have been added during fermentation to promote protein release to the extracellular medium (Aristidou et al., *Biotechnology Letters* 15: 331–336 (1993)). While partial release of several intracellular proteins has been reported, this approach requires direct coupling of fermentation and release strategies and subsequent separation of the protein of interest from a potentially complex extracellular broth.

Once the polypeptide of interest is released from the host cell, purification thereof from other cell components is required. Unfortunately, most extraction approaches, such as cell lysis, not only expose the protein to potential degradation by host cell proteases, but also make isolation of the protein from other elements of the resulting suspension more difficult. For example, the presence of negatively charged molecules, such as DNA, RNA, phospholipids, and lipopolysaccharides (LPS), often requires the use of anion-exchange chromatography (Sassenfeld, *TIBTECH*, 8: 88–93 (1990); Spears, *Biotechnology, vol. 3*—Bioprocessing, Rehm eds: 40–51 (1993)) and/or precipitation with polycations, such as protamine sulfate (Kelley et al., *Bioseparation*, 1: 333–349 (1991); Scopes, *Protein Purification Principles and Practice*, 2nd edition, Cantor eds., pp. 21–71 (1987)), streptomycin sulfate (Wang et al., eds, *Fermentation and Enzyme Technology:* 253–256 (1979)), polyethylenimine (PEI) (Kelley et al., supra; Sassenfeld; Cumming et al., *Bioseparation*, 6: 17–23 (1996); Jendrisak, *The use of polyethyleneimine in protein purification. Protein purification: micro to macro*, ed. Alan R., Liss, Inc, 75–97 (1987); Salt et al., *Enzyme and Microbial Technology*, 17: 107–113 (1995)), and/or aqueous two-phase extraction with immiscible polymer systems such as polyethylene glycol (PEG)/phosphate or PEG/dextran (Kelley et al., supra, Strandberg et al., *Process Biochemistry* 26: 225–234 (1991)).

Alternatively, the protein of interest may be precipitated away from non-proteinaceous polyanionic contaminants through the addition of a neutral salt such as ammonium sulfate or potassium chloride (Wheelwright, *Protein Purification: Design and Scale up of Downstream Processing:* 87–98 (1991); Englard et al., *Methods in Enzymology* Volume 182, Deutscher eds.: 285–300 (1990)) and/or a polymer such as PEG or dextran sulfate (Wang et al., supra; Wheelwright, supra). Where the protein of interest is positively charged, it will tend to bind to any negatively charged molecules present thereby, making purification of the protein virtually impossible.

Typically, researchers have utilized the initial fractionation steps, described above, to separate the offending polyanions from the protein of interest. Unfortunately, each of these initial separation methods suffers from severe disadvantages, especially when used in the manufacture of pharmaceutical reagents. For example, the large quantities of non-proteinaceous polyanionic contaminants found in bacterial lysates tend to reduce the binding capacities of anion-exchange chromatography resins. In addition, regeneration protocols are often rendered ineffective due to tenacious binding of the polyanions to the resins (Spears, supra). Finally, the low ionic strength conditions that favor protein binding are ineffective at disrupting polyanion-protein interactions and result in a lack of separation (Scopes, *Protein Purification Principles and Practice*, 3rd edition, Cantor eds., p. 171 (1994)). Protamine sulfate preparations are plagued by concerns over protease and viral contaminations. Moreover, unwanted protein precipitation can occur using this reagent (Scopes, *Protein Purification Principles and Practice*, 2nd edition, Cantor eds., 21–71 (1987)).

In the processing of pharmaceutical proteins, streptomycin sulfate is generally not used due to general apprehension over the use of antibiotics as process reagents (Scawen et al., *Handbook of Enzyme Biotechnology* 2nd edition, Wiseman eds.: 15–53 (1985)). PEI preparations are often contaminated with varying amounts of the ethylenimine monomer, a suspected cancer agent (Scawen et al., supra). PEI also tends to bind irreversibly to many chromatography resins, thereby limiting their effectiveness and the number of potential chromatography resins available for use post-PEI clarification. In general, aqueous two-phase extractions systems are difficult to predict and often require an empirical approach for determining conditions that move the protein of interest into the appropriate aqueous phase (Kelley et al., supra).

Techniques that specifically precipitate the protein of interest often result in the entrapment of the non-proteinaceous contaminants in the precipitate, rendering the separation ineffective (Scopes, supra; Wheelwright, supra).

Examples of patents describing protein recovery and purification include the following:

U.S. Pat. No. 5,665,866 discloses a process for obtaining antibodies in soluble and correctly folded and assembled form. It comprises a step to raise the operating temperature to from 34 to 60° C. at a time in the process selected to facilitate the subsequent isolation of soluble, correctly folded and assembled antibody, substantially free of other antibody-related material.

U.S. Pat. No. 5,760,189 discloses a method for releasing a thioredoxin-like fusion protein from *E. coli*, including negatively charged non-proteinaceous material, into a solution by adding chelator to the solution, and precipitating the negatively charged non-proteinaceous material from the solution by adding a divalent cation/alcohol solution to the solution to form a first soluble fraction containing the protein and a first insoluble fraction containing unwanted contaminants. Optionally, the temperature prior to the addition of chelator may be substantially cooler than after the addition of chelator. The divalent cation includes, for example, magnesium, manganese, and calcium, alone or in combination.

U.S. Pat. No. 5,714,583 discloses methods for the purification of factor IX in a solution comprising the steps of applying the solution containing factor IX to an anion-exchange resin, washing the anion-exchange resin with a solution having a conductivity that is less than required to elute factor IX from the resin, eluting the anion-exchange resin with a first eluant to form a first eluate, applying the eluate to a heparin or heparin-like (e.g., negatively charged matrix) resin, eluting the heparin or heparin-like resin with a second eluant to form a second eluate, applying the second eluate to an hydroxyapatite resin, and then eluting the hydroxyapatite resin with a third eluant to form a third eluate containing the purified factor IX.

U.S. Pat. No. 6,322,997 discloses a method for recovering a polypeptide comprising exposing a composition comprising a polypeptide to a reagent that binds to, or modifies, the polypeptide, wherein the reagent is immobilized on a solid phase; and then passing the composition through a filter bearing a charge that is opposite to the charge of the reagent in the composition, so as to remove leached reagent from the composition.

U.S. Pat. No. 6,214,984 discloses low-pH hydrophobic interaction chromatography (LPHIC) for antibody purification. In particular, the patent provides a process for purifying an antibody from a contaminant that comprises loading a mixture containing the antibody and the contaminant on a hydrophobic interaction chromatography column and eluting the antibody from the column with a buffer having a pH of about 2.5–4.5. Usually, the mixture loaded onto the column is at about the same pH as the elution buffer.

U.S. Pat. No. 6,121,428 provides a method for recovering a polypeptide comprising exposing a composition comprising a polypeptide to a reagent that binds to, or modifies, the polypeptide, wherein the reagent is immobilized on a solid phase; and then passing the composition through a filter bearing a charge that is opposite to the charge of the reagent in the composition, so as to remove leached reagent from the composition.

U.S. Pat. No. 5,641,870 provides a process for purifying an antibody, wherein a mixture containing the antibody and contaminant is subjected to LPHIC optionally at low salt concentration. The antibody is eluted from the column in the fraction that does not bind thereto. In the extraction step, frozen cell pellets are re-suspended at room temperature in 20 mM MES buffer, pH 6.0 containing 5 mM EDTA and 20 mM 4,4'-DTP previously dissolved in ethanol (3 liters of buffer/kg of cell pellet). The suspended cells are disrupted by two passages through a Mantin Gaulin homogenizer at 5500 to 6500 PSI. The homogenate is adjusted to 0.25% (v/v) with polyethyleneimine (PEI) and diluted with an equal volume of 2–8° C. purified water. The diluted homogenate is then centrifuged. The antibody fragment is found in the supernatant.

Historically, immunoglobulin G (IgG) has been purified from human serum and plasma (Putnam, ed, *The Plasma Proteins*, vol. 1 (Academic Press, 1975)). The purification process has often contained one or more precipitation steps The mast commonly used precipitation scheme for recovering IgG is the Cohn fractionation (Cohn et al., *J. Amer. Chem. Soc.*, 72: 465 (1950)). However, other precipitation techniques have been reported (Niederauer and Glatz, *Advances in Biochemical Engineering Biotechnology*, v. 47 (Springer-Verlag Berlin Heidelberg, 1992): Sternberg and Hershberger, *Biochim. et Biophys, Acta,* 342: 195–206 (1974)). The pioneering work of purifying IgG from plasma using 6,9-diamino-2-ethoxyacridine lactate (USAN name and herein called ethacridine lactate and also known by the names ETHODIN™ or RIVANOL™), a highly aromatic cationic dye, is reported by Horeisi and Smetana, *Acta Med. Scand.*, 155: 65 (1956). The following decade produced a number of publications showing the capability of 6,9-diamino-2-ethoxyacridifle lactate to purify IgG and other proteins (Miller, *Nature*, 184: 450 (1959); Steinbuch and Niewiarowski, *Nature,* 186: 87 (1960); Neurath and Brunner, *Experientia,* 25: 668 (1969)) from biological materials, e.g., plasma and growth media. Use of ethacridine lactate to recover antibodies and other proteins from other sources has been reported. See Tcbernov et al., *J. Biotechnol,* 69: 69–73 (1999): SU 944580 published 28 Jul. 1982; Franek and Dolnikova, *Biotech-Forum-Eur,* 7: 468–470 (1990); EP 250288 published 23 Dec. 1987; DE3604947 published 20 Aug. 1987; Rothwell et al., *Anal. Biochem.,* 149: 197–201 (1985); Lutsik and Antonyuk, *Biokhimiva,* 47: 1710–1715 (1982); and Aizenman et al., *Mikrobiol-Zh.,* 44: 69–72 (1982).

The primary step of recovering polypeptides from microorganisms is most often concerned with removing solid material, e.g., cells and cellular debris. It is important to recognize the need to separate the desired product from components present in conditioned medium with which it specifically interacts. Where the protein of interest is positively charged, it will tend to bind to any negatively charged molecules present, thereby making purification of the protein by traditional methods very difficult. Additional removal of contaminating soluble protein from crude microbial extracts, e.g., *E. coli* homogenate, during this step would simplify subsequent chromatography steps. Such additional removal would be especially valuable for industrial-scale production, resulting in decreased chromatography column size and production times.

SUMMARY OF THE INVENTION

The invention involving purification is as claimed.

Specifically, in one aspect, the invention provides a method for purifying a desired heterologous polypeptide from microbial fermentation broth or homogenate in which it is produced and solubilized comprising adding to the broth or homogenate an effective amount of a solution of 6,9-diamino-2-ethoxyacridine lactate (ethacridine lactate) to precipitate host cell impurities under conditions wherein the majority of the polypeptide remains soluble, and separating the desired polypeptide from the broth or homogenate.

In another aspect, the invention provides a microbial cell fermentation broth or homogenate comprising ethacridine lactate and a polypeptide heterologous to the cells.

Addition of ethacridine lactate as a precipitation agent unexpectedly results in a dramatic removal of host debris including host proteins. In this process, the majority of host proteins will be recovered in a precipitate together with the cell debris, and the polypeptide is recovered in the clarified supernatant. The improved purity of the clarified extract when using ethacridine lactate results in reduction in the volume of chromatographic media or resin required for the columns, thereby reducing the scale needed for subsequent purification. It also results in elimination of some chromatographic step(s), which improves processing time and cost. In addition, the process herein results in a stable feedstock and can be operated at a neutral pH.

BRIEF DESCRIPTION OF THE DRAWINGS

FIG. 1 is a schematic representation of the construction of the antiCD18 F(ab')$_2$(-leucine zipper) plasmids pS1130 (single promoter) and pxCD18-7T3 (dual-promoter).

FIG. 2 depicts the inserted nucleic acid sequence (designated as Anti-CD18-7T3.DNA; SEQ ID NO:1) of the dual-promoter construct pxCD18-7T3.

FIGS. 3A and 3B depict the amino acid sequences (designated in combination as Anti-CD18-7T3.Protein) encoded by the two translational units within the construct pxCD18-7T3 (SEQ ID NOS:2 and 3), designated as STII+Anti-CD18 light chain (FIG. 3A) and STII+Anti-CD18 heavy chain (FIG. 3B), respectively. N-terminal STII secretion signal sequences are underlined.

FIG. 4 is a schematic of the anti-Tissue Factor IgG1 plasmids paTF130 (phoA/phoA promoters) and pxTF-7T3FL (phoA/tacII-promoters).

FIG. 5 depicts the inserted nucleic acid sequence (designated as Anti-TF-7T3FL.DNA; SEQ ID NO:4) of the phoA/tacII-promoter construct pxTF-7T3FL.

FIGS. 6A and 6B depict the amino acid sequences (designated in combination as Anti-TF-7T3FL.Protein) encoded by the two translational units within the construct pxTF-7T3FL (SEQ ID NOS:5 and 6) designated as STII+Anti-TF light chain (FIG. 6A) and STII+Anti-TF heavy chain (FIG. 6B), respectively. N-terminal STII secretion signal sequences are underlined.

FIG. 11 shows a graph of solubility of ethacridine lactate at increasing sodium chloride concentrations. The samples were incubated for three hours at room temperature before the concentration of soluble ethacridine lactate was determined. The open keys symbolize the 1.2% ethacridine lactate solution and the closed keys the 0.6% solution. The solid line is the 0.6% ethacridine lactate solution at pH 6.0, the broken line is the 1.2% ethacridine lactate solution at pH 6, the dotted line is the 0.6% ethacridine lactate solution at pH 9, and the broken line with dots is the 1.2% ethacridine lactate solution at pH 9.

DETAILED DESCRIPTION OF THE PREFERRED EMBODIMENTS

Definitions

Figure 7:
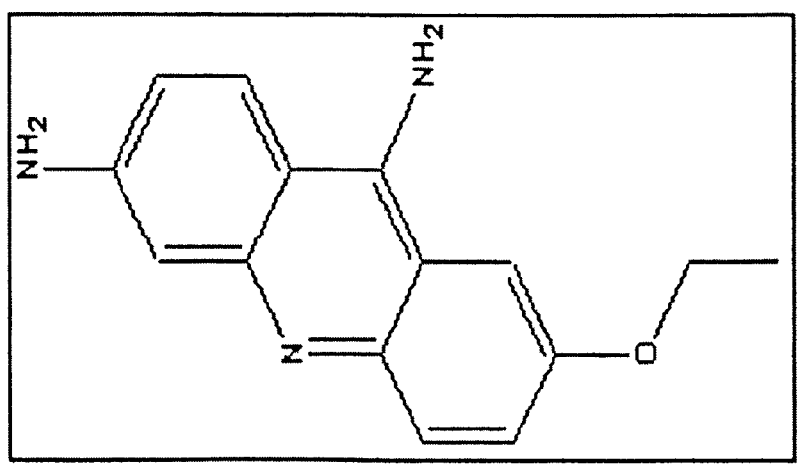
FIG. 7 depicts the chemical structure of ethacridine lactate.

The expression "microbial fermentation broth or homogenate" refers to broth, paste, or extract, preferably resuspended, obtained from microorganisms, including yeast, fungi, and prokaryotes such as bacteria, that are cultured and consuming nutrients, no matter what culturing vessel is utilized, for example, a shake flask or fermentor. Preferably, the broth or homogenate is from yeast or prokaryotes. More preferably, the broth or homogenate is from bacteria. Homogenate is preferred herein. In some cases if the solution has very high conductivity it may be preferred to harvest the cells and re-suspend them, but otherwise, it is preferred to use the homogenate as it is directly from the fermentor. The components of the broth or homogenate include cell debris, host cell protein, DNA, RNA, etc. Thus, the addition of the lactate herein leads to selective precipitation of host cell proteins, etc., giving better purification power than not using the lactate.

The expression "under conditions wherein the majority of the polypeptide remains soluble" refers to addition of ethacridine lactate to the broth or homogenate in amounts and at a temperature and conductivity level that prevent the majority of the target polypeptide from precipitating from the broth or homogenate. Preferably, such conditions prevent more than about 60% of the polypeptide from precipitating, more preferably more than about 70%, still more preferably more than about 75%, even more preferably more than about 80%, even still more preferably more than about 85%, and still more preferably more than about 85%, even still more preferably more than about 90%, and most preferably more than about 95%. This degree of solubility is measured by an appropriate assay, such as, for example, RP-HPLC, affinity chromatography, ELISAs, RIAs, and a combination of SDS-PAGE and high-performance affinity chromatography (HPAC). The choice of assay depends on such factors as the type of host cell used and polypeptide being produced.

The "bacteria" for purposes herein include *eubacteria* and *archaebacteria*. Preferred of these are *eubacteria*, including gram-positive and gram-negative bacteria. More preferred are gram-negative bacteria. One preferred type of bacteria is Enterobacteriaceae. Examples of bacteria belonging to Enterobacteriaceae include *Escherichia, Enterobacter, Erwinia, Klebsiella, Proteus, Salmonella, Serratia,* and *Shigella*. Other types of suitable bacteria include *Azotobacter, Pseudomonas, Rhizobia, Vitreoscilla,* and *Paracoccus. E. coli* is preferred herein. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting, and W3110 is preferred. Mutant cells of any of the above-mentioned bacteria may also be employed. It is, of course, necessary to select the appropriate bacteria taking into consideration replicability of the replicon in the cells of a bacterium. For example, *E. coli, Serratia,* or *Salmonella* species can be suitably used as the host when well-known plasmids such as pBR322, pBR325, pACYC177, or pKN410 are used to supply the replicon. See further below regarding examples of suitable bacterial host cells.

As used herein, the expressions "cell," "cell line," "strain," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polypeptide" refers generally to peptides and proteins from any cell source having more than about ten amino acids. "Heterologous" polypeptides are those polypeptides foreign to the host cell being utilized, such as a human protein produced by E. coli. While the heterologous polypeptide may be prokaryotic or eukaryotic, preferably it is eukaryotic, more preferably mammalian, and most preferably human. Preferably, it is a recombinantly produced, or recombinant polypeptide.

The polypeptide is produced and solubilized in the fermentation broth or homogenate, meaning that it is made in such broth or homogenate and is either already in a soluble fraction resulting from production, or is in an insoluble fraction or form or phase that is treated or contacted with a solubilizing agent such as a chaotrope (e.g., urea or guanidine) or detergent (such as sodium dodecyl sulfate (SDS)), with or without a reducing agent (such as dithiothreitol or beta-mercaptoethanol) so as to be solubilized. "Soluble," "solubilized," "solubilization," "dissolved," or "dissolution" in the sense used herein means that the polypeptide is in the supernatant rather than in the solids fraction after centrifugation. Precipitation or degree of solubility can be determined, for example, by the appropriate assays as noted above.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; 1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA) and variants thereof such as RETEVASE™ and TNKASE™; bombesin; thrombin; hemopoietic growth factor; tumor necrosis factor-alpha and -beta; antibodies to ErbB2 domain(s) such as 2C4 (WO 01/00245; hybridoma ATCC HB-12697), which binds to a region in the extracellular domain of ErbB2 (e.g., any one or more residues in the region from about residue 22 to about residue 584 of ErbB2, inclusive), enkephalinase; a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; serum albumin, such as human serum albumin (HSA) or bovine serum albumin (BSA); colony stimulating factors (CSFs), e.g., M-CSF, GM-CSF, and G-CSF; interleukins (ILs), e.g., IL-1 to IL-10; anti-HER-2 antibody; Apo2 ligand; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

Preferred polypeptides herein include human serum albumin (HSA), 2C4, tissue factor, anti-tissue factor, anti-CD20, anti-HER-2, heregulin, anti-IgE, anti-CD11a, anti-CD18, VEGF and receptors and antibodies thereto such as rhuFab V2 and AVASTIN™, growth hormone and its variants, such as hGH, growth hormone receptors, growth hormone releasing protein (GHRP), LIV-1 (EP 1,263,780), TRAIL, tumor necrosis factor (TNF) and antibodies thereto, TNF receptor and related antibodies, TNF-receptor-IgG, TNF receptor associated factors (TRAFs) and inhibitors thereof, Factor VIII, Factor VIII B domain, interferons such as interferon-gamma, transforming growth factors (TGFs) such as TGF-beta, anti-TGF such as anti-TGF-beta, activin, inhibin, anti-activin, anti-inhibin, tissue-plasminogen activators and their variants such as t-PA, RETEPLASE™, and TNKase, anti-Fas antibodies, Apo-2 ligand; Apo-2 ligand inhibitor; Apo-2 receptor, Apo-3, apoptotic factors, Ced-4, DcR3, death receptor and agonist antibodies (DR4, DR5), lymphotoxin (LT), prolactin, prolactin receptor, SOB proteins, WISP (wnt-induced secreted proteins), neurotoxin-3 (NT-3), nerve growth factor (NGF) and anti-NGF, DNase, hepatitis antigen, herpes simplex antigen, leptin, insulin-like growth factors (IGFs) such as IGF-1 and IGF-2 and their binding proteins and receptors such as IGFBP-1-IGFBP-6, insulin, fibroblast growth factors (FGFs) such as FGF-17, Toll protein, TIE ligands, CD40 and anti-CD40, immunoadhesins, subtilisin, hepatocyte growth factor (HGF), thrombopoietin (TPO), interleukins such as IL-2, IL-12, IL-17, IL-22, IL-8, IL-9, and antibodies thereto, and prostrate-specific cancer antigen (PSCA).

Examples of antibodies that bind HER2 include 4D5, 7C2, 7F3 and 2C4, as well as humanized variants thereof, including huMAb4D5-1, huMAb4D5-2, huMAb4D5-3, huMAb4D5-4, huMAb4D5-5, huMAb4D5-6, huMAb4D5-7 and huMAb4D5-8 as described in Table 3 of U.S. Pat. No. 5,821,337; and humanized 2C4 mutant nos. 560, 561, 562, 568, 569, 570, 571, 574, or 56869 as described in WO01/00245. 7C2 and 7F3 and humanized variants thereof are described in WO98/17797.

Examples of antibodies that bind the CD20 antigen include: "C2B8," which is now called "Rituximab" ("RITUXAN®") (U.S. Pat. No. 5,736,137); the yttrium-[90]-labeled 2B8 murine antibody designated "Y2B8" (U.S. Pat. No. 5,736,137); murine IgG2a "B1" optionally labeled with $^{131}$I to generate the "$^{131}$I-B1" antibody (BEXXAR™) (U.S. Pat. No. 5,595,721); murine monoclonal antibody "1F5" (Press et al., *Blood,* 69(2): 584–591 (1987)); "chimeric 2H7" antibody (U.S. Pat. No. 5,677,180); and monoclonal antibodies L27, G28-2, 93-1B3, B-C1 or NU-B2 available from the International Lenkocyte Typing Workshop (Valentine et al., In: *Leukocyte Typing III* (McMichael, Ed., p. 440, Oxford University Press (1987)).

More preferred polypeptides are 2C4, anti-tissue factor, anti-CD20, anti-HER-2, heregulin, anti-IgE, anti-CD11a, anti-CD18, anti-VEGF such as rhuFab V2, hGH, GHRP, LIV-1, TRAIL, antibodies to TNF and TNF receptor and related antibodies, inhibitors of TRAF, TNF-receptor-IgG, Factor VIII, Factor VIII B domain, interferon-gamma, TGF-beta and anti-TGF-beta, activin, inhibin, anti-activin, anti-inhibin, t-PA, TNKase, anti-Fas antibodies, Apo-2 ligand; Apo-2 ligand inhibitor; Apo-2 receptor, Apo-3, DcR3, death receptor and agonist antibodies (DR4, DR5), lymphotoxin (LT), prolactin, prolactin receptor, WISP, anti-NGF, NGF, NT-3, anti-IL-8, anti-IL-9. IL-17, IL-22, DNase, GHRP, hepatitis antigen, herpes simplex antigen, leptin, IGF-1 and IGFBP1-6, insulin, FGF-17, Toll protein, TIE ligands, CD40, immunoadhesins, subtilisin, HGF, and TPO.

Still more preferred polypeptides are 2C4, anti-tissue factor, anti-CD20, anti-HER-2, anti-IgE, anti-CD11a, anti-CD18, anti-VEGF such as rhuFab V2, hGH, LIV-1, TRAIL, antibodies to TNF and TNF receptor and related antibodies, TNF-receptor-IgG, Factor VIII, Factor VIII B domain, interferon-gamma, TGF-beta, activin, inhibin, anti-activin, anti-inhibin, t-PA, TNKase, Apo-2 ligand; Apo-2 ligand inhibitor; Apo-2 receptor, Apo-3, DcR3, death receptor and agonist antibodies (DR4, DR5), WISP, inhibitors of TRAF, anti-NGF, NGF, NT-3, anti-IL-8, anti-IL-9, IL-17, IL-22, anti-TGFs, DNase, GHRP, hepatitis antigen, herpes simplex antigen, leptin, IGF-1 and IGFBP1-6, insulin, FGF-17, Toll protein, TIE ligands, anti-CD40, HGF, and TPO.

Particularly preferred polypeptides are recombinant polypeptides, more preferably antibodies, which include monoclonal antibodies and humanized antibodies. Such antibodies may be full-length antibodies or antibody fragments. More preferably, these antibodies are human or humanized antibodies. These include, e.g., the particularly preferred polypeptides 2C4, anti-tissue factor Fab'2 and full-length, anti-CD20, anti-HER-2, anti-IgE, anti-CD11a, anti-CD18 Fab'2 and full-length, anti-VEGF full-length and rhuFab V2, LIV-1, DR4, DR5, and TRAIL.

Still more preferably, the antibody is an anti-IgE, anti-CD18, anti-VEGF, anti-tissue factor, 2C4, anti-Her-2, anti-CD20, anti-CD40, or anti-CD11a antibody. Antibody fragments encompassed within the definition of polypeptide preferably comprise a light chain, more preferably a kappa light chain. Such preferred fragments include, for example, a Fab, Fab', F(ab')$_2$, or F(ab')$_2$-leucine zipper (LZ) fusion, and most preferably are F(ab')$_2$. The most preferred antibodies are anti-CD18 F(ab')$_2$, anti-tissue factor F(ab')$_2$, full-length anti-tissue factor antibody, and anti-VEGF antibody.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Koehler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624–628 (1991) and Marks et al. J. Mol. Biol., 222: 581–597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81: 6851–6855 (1984)). Chimeric antibodies of interest herein include "primatized" antibodies comprising variable-domain antigen-binding sequences derived from a non-human primate (e.g. Old World Monkey, Ape etc) and human constant-region sequences.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact" antibody is one that comprises an antigen-binding variable region as well as a light-chain constant domain ($C_L$) and heavy-chain constant domains, $C_H1$, $C_H2$ and $C_H3$. The constant domains may be native-sequence constant domains (e.g. human native-sequence constant domains) or amino acid sequence variants thereof. Preferably, the intact antibody has one or more effector functions.

Antibody "effector functions" refer to those biological activities attributable to the Fc region (a native-sequence Fc region or Fc region with amino acid sequence variation) of an antibody. Examples of antibody effector functions include C1q binding, complement dependent cytotoxicity, Fc receptor binding, antibody-dependent cell-mediated cytotoxicity (ADCC), phagocytosis, down-regulation of cell-surface receptors (e.g. B cell receptor; BCR), etc.

Depending on the amino acid sequence of the constant domain of their heavy chains, intact antibodies can be assigned to different "classes". There are five classes of immunoglobulins: IgA, IgD, IgE, IgG, and IgM, having heavy chains designated $\alpha$, $\delta$, $\epsilon$, $\gamma$, and $\mu$, respectively. The $\gamma$ and $\alpha$ classes are further divided into subclasses on the basis of relatively minor differences in CH sequence and function, e.g., humans express the following subclasses: IgG1, IgG2, IgG3, IgG4, IgA1, and IgA2. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcRIII only, whereas monocytes express FcRI, FcRII and FcRIII. FcR expression on hematopoietic cells is summarized in Table 3 on page 464 of Ravetch and Kinet, *Annu. Rev. Immunal*, 9: 457–492 (1991). To assess ADCC activity of a molecule of interest, an in vitro ADCC assay, such as that described in U.S. Pat. No. 5,500,362 or 5,821,337, may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Natl. Acad. Sci. USA*, 95: 652–656 (1998).

"Human effector cells" are leukocytes that express one or more FcRs and perform effector functions. Preferably, the cells express at least FcRIII and perform ADCC effector function. Examples of human leukocytes that mediate ADCC include peripheral blood mononuclear cells (PBMC), natural killer (NK) cells, monocytes, cytotoxic T cells, and neutrophils, with PBMCs and NK cells being preferred. The effector cells may be isolated from a native source thereof, e.g. from blood or PBMCs as described herein.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light-chain and the heavy-chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming, part of the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody-dependent cellular cytotoxicity (ADCC).

The term "hypervariable region" when used herein refers to the amino acid residues of an antibody that are responsible for antigen binding. The hypervariable region generally comprises amino acid residues from a "complementarity-determining region" or "CDR" (e.g. residues 24–34 (L1), 50–56 (L2) and 89–97 (L3) in the light-chain variable domain and 31–35 (H1), 50–65 (H2) a the heavy-chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26–32 (L1), 50–52 (L2) and 91–96 (L3) variable domain and 26–32 (H1), 53–55 (H2) and 96–101 (H3) in the heavy-chain variable do Chothia and Lesk, *J. Mol. Biol.*, 196: 901–917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-binding sites and is still capable of cross-linking antigen.

"Fv" is the minimum antibody fragment that contains a complete antigen-recognition and antigen-binding site. This region consists of a dimer of one heavy-chain and one light-chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy-chain CH1 domain including one or more cysteines from the antibody hinge region. Fab'-SH is the designation herein for Fab' in which the cysteine residue(s) of the constant domains bear at least one free thiol group. $F(ab')_2$ antibody fragments originally were produced as pairs of Fab' fragments that have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains that enables the scFv to form the desired structure for antigen binding. For a review of scFv, see Plückthun in *The Pharmacology of Monoclonal Antibodies*, vol. 113, Rosenburg and Moore eds. (Springer-Verlag, New York, 1994), pp. 269–315. Anti-ErbB2 antibody scFv fragments are described in WO93/16185; U.S. Pat. No. 5,571,894; and U.S. Pat. No. 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90: 6444–6448 (1993).

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody), such as mouse, rat, rabbit, or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature,* 321: 522–525 (1986); Riechmann et al., *Nature,* 332: 323–329 (1988); and Presta, *Curr. Op. Struct. Biol.,* 2: 593–596 (1992).

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells, since at least one component of the antibody's natural environment will not be present. Ordinarily, however, isolated antibody will be prepared by at least one purification step.

A "leucine zipper" is a peptide (often about 20–40 amino acid residues long) having several repeating amino acids, in which every seventh amino acid is a leucine residue. Such leucine zipper sequences form amphipathic alpha-helices, with the leucine residues lined up on the hydrophobic side for dimer formation. Examples of leucine zippers herein include the Fos-Jun leucine zipper (O'Shea et al., *Science,* 245: 646 (1989)), which may be used for forming heterodimers (e.g. bispecific antibodies); the GCN4 leucine zipper from yeast (Landschulz et al., *Science,* 240: 1759–1764 (1988)) which may be used for forming homodimers (e.g., monospecific antibodies); and leucine zippers found in other DNA-binding proteins, such as C/EBP and c-myc, as well as variants of any of these.

The expression "control sequences" refers to DNA sequences necessary for the expression of an operably linked coding sequence in a particular host organism. The control sequences that are suitable for bacteria include a promoter, optionally an operator sequence, and a ribosome-binding site.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. Linking is accomplished, for example, by ligation at convenient restriction sites. If such sites do not exist, the synthetic oligonucleotide adaptors or linkers are used in accordance with conventional practice.

The term "recovery" of a polypeptide generally means obtaining the polypeptide free from the cells in which it was produced.

"Host cell impurities" means contaminating host proteins and other biomolecular impurities such as DNA and cell debris in the fermentation broth or homogenate.

Modes for Carrying Out the Invention

The invention provides in one aspect a method for purifying a desired heterologous polypeptide from a microbial fermentation broth or homogenate in which it is produced and solubilized. The polypeptide may already be produced in a soluble fraction, or it may be insoluble (e.g., produced in an insoluble fraction, phase, or form) and therefore contacted or treated so as to dissolve the polypeptide. If the polypeptide is produced in an insoluble state, it is solubilized by exposure to or contact with a solubilizing agent (as noted above) before the ethacridine lactate is added, for example, adding such agent to a fraction containing the insoluble polypeptide. It is preferred that the polypeptide is already in the soluble fraction. The method herein involves adding to the broth or homogenate an effective amount of a solution of ethacridine lactate to precipitate host cell impurities contained in the broth or homogenate. Such addition takes place under conditions wherein the majority of the polypeptide remains soluble. In the next step the desired polypeptide is separated from the broth or homogenate, including cell debris, host cell protein, DNA, RNA, etc.

Because most host proteins precipitated by the ethacridine lactate have a negative charge while the target polypeptide has a positive surface charge, it is preferred that the target polypeptide have a higher pI than the average pI of host proteins contained in the host cell impurities, so that it can be recovered in the supernatant from the precipitated host proteins. Such average pI can be determined by a 2-D gel of the host proteins, wherein, for example, the band of pI ranges from about 7.5 to 5.0, the average being 6.25. Alternatively, isoelectrofocusing alone (which is the first dimension on a 2-D gel) can be used for this determination, as well as chromatofocusing, and calculations by amino acid composition. The more preferred polypeptides are those having a pI of at least about 7, and preferably about 7–10.

The preferred polypeptides to be employed are set forth above.

The concentration of ethacridine lactate employed is dependent, for example, on the amount of negative charges in solution, which are on the surface of most host cell impurities present in the solution. Hence, the ethacridine lactate concentration depends at least on the amount of host cell impurities such as the DNA and host protein concentration in the solution. The higher the concentration of host protein and DNA in the homogenate, the higher the amount of ethacridine lactate required. Hence, the more negatively charged components available for the ethacridine lactate to complex with and thus precipitate, the higher amount of ethacridine lactate needed to maximize precipitation. The preferred concentration of ethacridine lactate is generally more than about 0.1% weight/volume. More preferred is an ethacridine lactate concentration of about 0.1–5%, still more preferred about 0.4–5%, and most preferably about 0.6–5% weight/volume.

In general, the lower the conductivity of the solution when performing the precipitation, the more efficient the purification of the polypeptide from the cell debris and DNA. The conductivity can be controlled, for example, by the amount of salt in the homogenate or broth or by diluting the homogenate or broth with water or other suitable solvent. It is preferred that the conductivity of the broth or homogenate after addition of the ethacridine lactate is less than about 16 milliSiemens (mS), more preferably about 1–15 mS, still more preferably about 1–10 mS, and most preferably about 1–5 mS.

The conductivity of the solution during the precipitation will depend at least in part on the type of salt present therein. Halides (e.g., chlorides or bromides) are not preferred anions for the salts, but if they are present, they are preferably at a concentration of less than about 100 mM in solution before adding the ethacridine lactate, and below about 50 mM once the ethacridine lactate is added. Some exemplary salts to employ herein include buffer salts, TRIS, MES, MOPS, acetate, and citrate. The concentration of salts present must not be above an amount that would precipitate the ethacridine lactate. The exact amount is dependent mainly on the type of salt and the stoichiometry between the salt and ethacridine lactate, and the limit is at the low end of the stoichiometry, i.e., the low end means more salt relative to the ethacridine lactate.

The pH of the broth or homogenate after addition of the ethacridine lactate depends, for example, on the pI of the polypeptide, the amount of negative surface charges on the polypeptide, the amount of host cell impurities in the solution, and the concentration of ethacridine lactate. The pH is preferably not higher than the pI of the polypeptide. Generally, the pH range is about 4–10; however, for efficient host cell impurity precipitation, the pH of the broth or homogenate after addition of the ethacridine lactate is preferably no greater than about 9, since the ethacridine lactate becomes less charged above this pH, with the preferred range of about 4–9. More preferably the pH of the broth or homogenate after addition of the ethacridine lactate is about 5–9, and still more preferably, about 6–9. The more negative surface charges on the polypeptide, the lower the pH within this range, with a preferred range for such polypeptides of about pH 6–7.

The broth or homogenate after addition of the ethacridine lactate optionally is incubated at an elevated temperature for a period of time. Whether to raise the temperature and for how long depends on many factors, including the type of polypeptide of interest, what, if any, modifications to the polypeptide of interest occur if exposed to elevated temperature during this period in the process, etc. For example, for the anti-tissue factor $F(ab')_2$ purifications, elevated temperatures are preferred, whereas for full-length antibody, it is preferred to have no heat or have the temperature no higher than about 25° C. With these factors in mind, in general, the temperature of the broth or homogenate after addition of the ethacridine lactate ranges from about room temperature to about 70° C., more preferably, from about room temperature to about 65° C. held for about 1–60 minutes. If the temperature should be elevated, one preferred range is from about 50 to 65° C. held for about 1–60 minutes.

In another aspect, the invention provides a composition of matter that is a fermentation broth or homogenate from microbial cells comprising ethacridine lactate and heterologous polypeptide. Preferably, the polypeptide is dissolved in such broth or homogenate. The cells, polypeptide, concentration, and conditions for the broth or homogenate are as indicated above. The dissolution degree of the polypeptide can be determined by an appropriate assay such as the assays as noted above. Culturing parameters are used and polypeptide production is conducted in a conventional manner, such as those procedures described below.

A. Selection of Nucleic Acid and Modifications Thereof

While the polypeptide herein, such as an antibody, may be produced from any source (e.g., peptic cleavage of intact antibodies), preferably it is made recombinantly. The nucleic acid encoding the polypeptide of interest is suitably RNA, cDNA, or genomic DNA from any source, provided it encodes the polypeptide(s) of interest. Methods are well known for selecting the appropriate nucleic acid for expression of heterologous polypeptides (including variants thereof) in microbial hosts. Selection of appropriate nucleic acid to prepare non-antibody polypeptides in microbial cell culture is well known in the art.

If monoclonal antibodies are being produced, DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transformed into the microbial host cells herein to obtain the synthesis of monoclonal antibodies in the recombinant host cells. Review articles on recombinant expression in bacteria of DNA encoding the antibody include Skerra et al., *Curr. Opinion in Immunol.*, 5: 256–262 (1993) and Pluckthun, *Immunol. Revs.*, 130: 151–188 (1992).

Methods for humanizing non-human antibodies have been described in the art. Preferably, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature*, 321: 522–525 (1986); Riechmann et al., *Nature*, 332: 323–327 (1988); Verhoeyen et al., *Science*, 239: 1534–1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.*, 151: 2296 (1993); Chothia et al., *J. Mol. Biol.* 196: 901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89: 4285 (1992); Presta et al., *J. Immunol.*, 151: 2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of the humanized antibody or affinity-matured antibody are contemplated. For example, the humanized antibody or affinity-matured antibody may be an antibody fragment, such as a Fab, that is optionally conjugated with one or more targeting agent(s) in order to generate an immunoconjugate. Alternatively, the humanized antibody or affinity-matured antibody may be an intact antibody, such as an intact IgG1 antibody.

Fab'-SH fragments can be directly recovered from *E. coli* and chemically coupled to form F(ab')$_2$ fragments (Carter et al., *Bio/Technology*, 10: 163–167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single-chain Fv fragment (scFv) (WO 93/16185; U.S. Pat. Nos. 5,571,894 and 5,587,458). The antibody fragment may also be a "linear antibody", e.g., as described in U.S. Pat. No. 5,641,870. Such linear antibody fragments may be monospecific or bispecific.

Bispecific antibodies are antibodies that have binding specificities for at least two different epitopes. Exemplary bispecific antibodies may bind to two different epitopes of the Dkk-1 protein. Bispecific antibodies can be prepared as full-length antibodies or antibody fragments (e.g., F(ab')$_2$ bispecific antibodies).

According to a different approach, antibody variable domains with the desired binding specificities (antibody-antigen combining sites) are fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding, present in at least one of the fusions. DNAs encoding the immunoglobulin heavy-chain fusions and, if desired, the immunoglobulin light chain, are inserted into separate expression vectors, and are co-transfected into a suitable bacterial host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121: 210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed, e.g., in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab'-SH fragments can be directly recovered from *E. coli* and chemically coupled to form bispecific antibodies (Shalaby et al., *J. Exp. Med.*, 175: 217–225 (1992)).

Various techniques for making and isolating bispecific antibody fragments directly from recombinant cell culture have also been described. For example, bispecific antibodies have been produced using leucine zippers (Kostelny et al., *J. Immunol.*, 148: 1547–1553 (1992)). The leucine zipper peptides from the Fos and Jun proteins are linked to the Fab' portions of two different antibodies by gene fusion. The antibody homodimers are reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90: 6444–6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported (Gruber et al., *J. Immunol.*, 152: 5368 (1994)).

Antibodies with more than two valencies are contemplated. For example, trispecific antibodies can be prepared (Tutt et al., *J. Immunol.*, 147: 60 (1991)).

Nucleic acid molecules encoding polypeptide variants are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, or cassette mutagenesis of an earlier prepared variant or a non-variant version of the polypeptide.

It may be desirable to modify the antibody of the invention with respect to effector function, e.g., so as to enhance Fc receptor binding. This may be achieved by introducing one or more amino acid substitutions into an Fc region of the antibody. Alternatively or additionally, cysteine residue(s) may be introduced in the Fc region, thereby allowing interchain disulfide bond formation in this region.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Other modifications of the antibody are contemplated herein. For example, the antibody may be linked to one of a variety of non-proteinaceous polymers, e.g., polyethylene glycol, polypropylene glycol, polyoxyalkylenes, or copolymers of polyethylene glycol and polypropylene glycol.

B. Insertion of Nucleic Acid Into a Replicable Vector

The heterologous nucleic acid (e.g., cDNA or genomic DNA) is suitably inserted into a replicable vector for expression in the microorganism under the control of a suitable promoter. Many vectors are available for this purpose, and selection of the appropriate vector will depend mainly on the size of the nucleic acid to be inserted into the vector and the particular host cell to be transformed with the vector. Each vector contains various components depending on the particular host cell with which it is compatible. Depending on the particular type of host, the vector components generally include, but are not limited to, one or more of the following: a signal sequence, an origin of replication, one or more marker genes, a promoter, and a transcription termination sequence.

In general, plasmid vectors containing replicon and control sequences that are derived from species compatible with the host cell are used in connection with microbial hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene*, 2: 95 (1977)). pBR322 contains genes for ampicillin and tetracycline resistance and thus provides easy means for identifying transformed cells. The pBR322 plasmid, or other bacterial plasmid or phage, also generally contains, or is modified to contain, promoters that can be used by the host for expression of the selectable marker genes.

(i) Signal Sequence Component

The DNA encoding the polypeptide of interest herein may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell.

For prokaryotic host cells that do not recognize and process the native or a eukaryotic polypeptide signal sequence, the signal sequence may be substituted by a prokaryotic signal sequence selected, for example, from the group consisting of the lamB, ompF, alkaline phosphatase, penicillinase, lpp, or heat-stable enterotoxin II leaders. For yeast secretion the signal sequence may be, e.g., the yeast invertase leader, alpha-factor leader (including *Saccharomyces* and *Kluyveromyces* alpha-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990.

(ii) Origin of Replication Component

Expression vectors contain a nucleic acid sequence that enables the vector to replicate in one or more selected host cells. Such sequences are well known for a variety of microbes. The origin of replication from the plasmid pBR322 is suitable for most Gram-negative bacteria such as *E. coli*.

(iii) Selection Gene Component

Expression vectors generally contain a selection gene, also termed a selectable marker. This gene encodes a protein necessary for the survival or growth of transformed host cells grown in a selective culture medium. Host cells not transformed with the vector containing the selection gene will not survive in the culture medium. This selectable marker is separate from the genetic markers as utilized and defined by this invention. Typical selection genes encode proteins that (a) confer resistance to antibiotics or other toxins, e.g., ampicillin, neomycin, methotrexate, or tetracycline, (b) complement auxotrophic deficiencies other than those caused by the presence of the genetic marker(s), or (c) supply critical nutrients not available from complex media, e.g., the gene encoding D-alanine racemase for Bacilli.

One example of a selection scheme utilizes a drug to arrest growth of a host cell. In this case, those cells that are successfully transformed with the nucleic acid of interest produce a polypeptide conferring drug resistance and thus survive the selection regimen. Examples of such dominant selection use the drugs neomycin (Southern et al., *J. Molec. Appl. Genet.*, 1: 327 (1982)), mycophenolic acid (Mulligan et al., *Science* 209: 1422 (1980)) or hygromycin (Sugden et al., *Mol. Cell. Biol.*, 5: 410–413 (1985)). The three examples given above employ bacterial genes under eukaryotic control to convey resistance to the appropriate drug G418 or neomycin (geneticin), xgpt (mycophenolic acid), or hygromycin, respectively.

(iv) Promoter Component

The expression vector for producing the polypeptide of interest contains a suitable promoter that is recognized by the host organism and is operably linked to the nucleic acid encoding the polypeptide of interest. Promoters suitable for use with prokaryotic hosts include the beta-lactamase and lactose promoter systems (Chang et al., *Nature*, 275: 615 (1978); Goeddel et al., *Nature*, 281: 544 (1979)), the arabinose promoter system (Guzman et al., *J. Bacteriol.*, 174: 7716–7728 (1992)), alkaline phosphatase, a tryptophan (trp) promoter system (Goeddel, *Nucleic Acids Res.*, 8: 4057 (1980) and EP 36,776) and hybrid promoters such as the tac promoter (deBoer et al., *Proc. Natl. Acad. Sci. USA*, 80: 21–25 (1983)). However, other known bacterial promoters are suitable. Their nucleotide sequences have been published, thereby enabling a skilled worker operably to ligate them to DNA encoding the polypeptide of interest (Siebenlist et al, *Cell*, 20: 269 (1980)) using linkers or adaptors to supply any required restriction sites.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

Promoters suitable for use in yeast are well known in the art. Examples of suitable promoting sequences for use with yeast hosts include the promoters for 3-phosphoglycerate kinase (Hitzeman et al., *J. Biol. Chem.*, 255: 2073 (1980)) or other glycolytic enzymes (Hess et al., *J. Adv. Enzyme Reg.*, 7: 149 (1968); Holland, *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

(v) Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) or other strains, and successful transformants are selected by ampicillin or tetracycline resistance where appropriate. Plasmids from the transformants are prepared, analyzed by restriction endonuclease digestion, and/or sequenced by the method of Sanger et al., *Proc. Natl. Acad. Sci. USA*, 74: 5463–5467 (1977) or Messing et al., *Nucleic Acids Res.*, 9: 309 (1981), or by the method of Maxam et al., *Methods in Enzymology*, 65: 499 (1980).

C. Selection and Transformation of Host Cells

Suitable host cells for cloning or expressing the DNA in the vectors herein are any microbial cells, including prokaryotes and fungal cells, including yeast. Suitable prokaryotes for this purpose include bacteria as defined above, preferably *eubacteria*, such as Gram-negative or Gram-positive organisms. Examples include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One preferred *E. coli* cloning host is *E. coli* 294 (ATCC 31, 446), although other strains such as *E. coli* B, *E. coli* X1776 (ATCC 31,537), and *E. coli* W3110 (ATCC 27,325) are suitable. These examples are illustrative rather than limiting. Mutant cells of any of the above-mentioned strains may also be employed as the starting hosts that are then further mutated to contain at least the minimum genotype required herein.

*E. coli* strain W3110 is a preferred parental *E. coli* host because it is a common host strain for recombinant DNA product fermentations. Examples of starting *E. coli* hosts to be used as parent hosts, along with their genotypes, are included in the table below:

| Strain | Genotype |
|---|---|
| W3110 | K-12 F lambda IN(rrnD-rrnE)1 |
| 1A2 | W3110 ΔfhuA |
| 9E4 | W3110 ΔfhuA ptr3 |
| 27A7 | W3110 ΔfhuA ptr3 phoAΔE15 Δ(argF-lac)169 |
| 27C6 | W3110 ΔfhuA ptr3 phoAΔE15 Δ(argF-lac)169 ΔompT |
| 27C7 | W3110 ΔfhuA ptr3 phoAΔE15 Δ(argF-lac)169 ΔompT degP41::kan$^R$ |
| 33D3 | W3110 ΔfhuA ptr3 lacIq lacL8 ΔompT degP41:: kan$^R$ |
| 36F8 | W3110 ΔfhuA phoAΔE15 Δ(argF-lac)169 ptr3 degP41:: kan$^R$ ilvG2096 |

-continued

| Strain | Genotype |
| --- | --- |
| 41H1 | W3110 ΔfhuA phoS* (T104) Δ(argF-lac)169 degP41:: kan$^R$ ptr3 ilvG2096(Val$^r$) |
| 43D3 | W3110 ΔfhuA ptr3 phoAΔE15 Δ(argF-lac)169 ΔompT degP41 kan$^R$ ilvG2096 |
| 43H1 | W3110 ΔfhuA phoAΔE15 Δ(argF-lac) 169 degP41ilvG2096(Val$^r$) ptr3 ΔompT prc::kan$^R$ sprW148R |
| 43E7 | W3110 ΔfhuA Δ(argF-lac)169 ΔompT ptr3 phoAΔE15 degP41ilvG2096 |
| 44D6 | W3110 ΔfhuA ptr3 Δ(argF-lac)169 degP41:: kan$^R$ ΔompT ilvG2096 |
| 45F8 | W3110 ΔfhuA ptr3 Δ(argF-lac)169 degP41 ΔompT phoS* (T10Y) ilvG2096 |
| 45F9 | W3110 ΔfhuA ptr3 Δ(argF-lac)169 degP41 ΔompT ilvG2096 phoS* (T10Y) Δcyo::kan$^R$ |
| 49A5 | W3110 ΔfhuA phoA ΔE15Δ(argF-lac)169 deoC2 degP41 ilvG2096 (Val$^r$) ΔfucP ΔmalE |
| 58B3 | W3110 ΔfhuA phoAΔE15 Δ(argF-lac)169 deoC degP41 ilvG2096(Val$^r$) Δprc |
| 58H2 | W3110 ΔfhuA phoAΔE15 Δ(argF-lac)169 degP41ilvG2096(Val$^r$) ptr3 ΔompT sprW148R |
| 58H7 | W3110 ΔfhuA (ΔtonA) Δ ptr3 ΔompT ΔdegP lac Iq ΔlacY |
| 59A7 | W3110 ΔfhuA phoAΔE15 Δ(argF-lac)169 deoC degP41 ilvG2096(Val$^r$) Δprc sprW148R |
| 60H4 | W3110 ΔfhuAΔmanA phoAΔE15 Δ(argF-lac)169 deoC2 degP41 ilvG2096(Val$^r$) Δprc prc-suppressor |
| 61D6 | W3110 ΔfhuA ptr3 lac Iq lacL8 ΔompTΔ(nmpc-fepE) degP41 |
| 62A7 | W3110 ΔfhuA ptr3 lac Iq lacL8 ΔompTΔ(nmpc-fepE) degP41 ilvG2096 |

Also suitable are the intermediates in making strain 36F8, i.e., 27B4 (U.S. Pat. No. 5,304,472) and 35E7 (a spontaneous temperature-resistant colony isolate growing better than 27B4). An additional suitable strain is the *E. coli* strain having the mutant periplasmic protease(s) disclosed in U.S. Pat. No. 4,946,783 issued Aug. 7, 1990.

The above strains may be produced by chromosomal integration of the parental strain or other techniques, including those set forth in the Examples below.

Full-length antibodies may be made in *E. coli* in accordance with the teachings of WO 02/061090 published Aug. 8, 2002.

In addition to prokaryotes, eukaryotic microbes such as filamentous fungi or yeast are suitable expression hosts for polypeptide-encoding vectors. *Saccharomyces cerevisiae* is a commonly used lower eukaryotic host microorganism. Others include *Schizosaccharomyces pombe* (Beach and Nurse, *Nature,* 290: 140 (1981); EP 139,383 published 2 May 1985); *Kluyveromyces* hosts (U.S. Pat. No. 4,943,529; Fleer et al., *Bio/Technology,* 2: 968–975 (1991)) such as, e.g., *K. lactis* (MW98-8C, CBS683, CBS4574; Louvencourt et al., *J. Bacteriol.,* 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8: 135 (1990)), *K. thermotolerans,* and *K. marxianus; yarrowia* (EP 402, 226); *Pichia pastoris* (EP 183,070; Sreekrishna et al., *J. Basic Microbiol.,* 28: 265–278 (1988)); *Candida; Trichoderma reesia* (EP 244,234); *Neurospora crassa* (Case et al., *Proc. Natl. Acad. Sci. USA,* 76: 5259–5263 (1979)); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112: 284–289 (1983); Tilburn et al., *Gene,* 26: 205–221 (1983); Yelton et al., *Proc. Natl. Acad. Sci. USA,* 81: 1470–1474 (1984)) and *A. niger* (Kelly and Hynes, *EMBO J.,* 4: 475–479 (1985)). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula*. A list of specific species that are exemplary of this class of yeasts may be found in C. Anthony, *The Biochemistry of Methylotrophs,* 269 (1982).

The nucleic acid encoding the polypeptide is inserted into the host cells. Preferably, this is accomplished by transforming the host cells with the above-described expression vectors and culturing in conventional nutrient media modified as appropriate for inducing the various promoters.

Depending on the host cell used, transformation is done using standard techniques appropriate to such cells. The calcium treatment employing calcium chloride, as described in section 1.82 of Sambrook et al., *Molecular Cloning: A Laboratory Manual* (New York: Cold Spring Harbor Laboratory Press, 1989), is generally used for prokaryotic cells or other cells that contain substantial cell-wall barriers. Another method for transformation employs polyethylene glycol/DMSO, as described in Chung and Miller, *Nucleic Acids Res.,* 16: 3580 (1988). Transformations into yeast are typically carried out according to the method of Van Solingen et al., *J. Bact.,* 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyornithine, may also be used.

D. Culturing the Host Cells

Prokaryotic cells used to produce the polypeptides of the invention are grown in media known in the art and suitable for culture of the selected host cells, including the media generally described by Sambrook et al., supra. Media that are suitable for bacteria include, but are not limited to, AP5 medium, nutrient broth, Luria-Bertani (LB) broth, Neidhardt's minimal medium, and C.R.A.P. minimal or complete medium, plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene. Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol, and dithiothreitol.

Examples of suitable media are given in U.S. Pat. Nos. 5,304,472 and 5,342,763. C.R.A.P. phosphate-limiting media consists of 3.57g $(NH_4)_2(SO_4)$, 1.07 g NaCitrate-$2H_2O$, 1.07 g KCl, 5.36 g Yeast Extract (certified), 5.36 g HycaseSF™-Sheffield, adjusted pH with KOH to 7.3, qs to 872 ml with SQ $H_2O$ and autoclaved; cooled to 55° C. and supplemented with 110 ml 1 M MOPS pH 7.3, 11 ml 50% glucose, 7 ml 1M) $Mg(SO_4)$. Carbenicillin may then be added to the induction culture at a concentration of 50 ug/ml.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C.

Where the alkaline phosphatase promoter is employed, *E. coli* cells used to produce the polypeptide of interest of this invention are cultured in suitable media in which the alkaline phosphatase promoter can be partially or completely induced as described generally, e.g., in Sambrook et al., supra. The culturing need never take place in the absence of inorganic phosphate or at phosphate starvation levels. At first, the medium contains inorganic phosphate in an amount above the level of induction of protein synthesis and sufficient for the growth of the bacterium. As the cells grow and utilize phosphate, they decrease the level of phosphate in the medium, thereby causing induction of synthesis of the polypeptide.

If the promoter is an inducible promoter, for induction to occur, typically the cells are cultured until a certain optical density is achieved, e.g., a $A_{550}$ of about 200 using a high cell density process, at which point induction is initiated (e.g., by addition of an inducer, by depletion of a medium component, etc.), to induce expression of the gene encoding the polypeptide of interest.

Any necessary supplements may also be included at appropriate concentrations that would be known to those skilled in the art, introduced alone or as a mixture with another supplement or medium such as a complex nitrogen source. The pH of the medium may be any pH from about 5–9, depending mainly on the host organism. For *E. coli*, the pH is preferably from about 6.8 to about 7.4, and more preferably about 7.0.

One selective media that can be used for culturing yeast is a synthetic complete dextrose agar lacking uracil (SCD-Ura) prepared as described in Kaiser et al., *Methods in Yeast Genetics* (Cold Spring Harbor Press, Cold Spring Harbor, N.Y., 1994), p. 208–210.

E. Detecting Expression

Gene expression may be measured in a sample directly, for example, by conventional Southern blotting, northern blotting to quantitate the transcription of mRNA (Thomas, *Proc. Natl. Acad. Sci. USA*, 77: 5201–5205 (1980)), dot blotting (DNA analysis), or in situ hybridization, using an appropriately labeled probe, based on the sequences of the polypeptide. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, assays or gels may be employed for detection of protein.

F. Purification of Polypeptides

When using recombinant techniques, the polypeptide herein is produced intracellularly or in the periplasmic space. If the polypeptide is produced intracellularly, as a first step, the particulate debris, either host cells or lysed cells (e.g. resulting from homogenization), is removed, for example, by centrifugation or ultrafiltration, to produce a cell broth or homogenate.

Then, in accordance with this invention, the cellular impurities as defined above are removed from the homogenate or broth by precipitation using the ethacridine lactate under the conditions as set forth above, and the resulting mixture is treated so that the polypeptide of interest, in soluble form, is recovered.

The separation of the target polypeptide from the broth or homogenate may be accomplished by any suitable means, including those well known in the art such as centrifugation and filtration. Preferably, the separation is performed using centrifugation or tangential flow filtration, for example, using a filter of about 300 kiloDaltons to 1 micron.

After the polypeptide is separated from the broth or homogenate, it may be purified by any known means, including chromatography or filtration such as ultrafiltration/diafiltration or tangential flow filtration. In particular, the following procedures, individually or in combination, are exemplary of suitable purification procedures, with the specific method(s) used being dependent on the type of polypeptide: immobilized metal affinity chromatography (IMAC), aqueous two-phase separation (ATPS), fractionation on immunoaffinity or ion-exchange columns; ethanol precipitation; reversed-phase HPLC; hydrophobic-interaction chromatography (HIC); chromatography on silica; chromatography on an ion-exchange resin such as S-SEPHAROSE™ and DEAE; chromatofocusing; SDS-PAGE; ammonium-sulfate precipitation; ultrafiltration/diafiltration, tangential flow filtration, and gel filtration using, for example, SEPHADEX™ G-75.

For example, as part of the overall recovery process for the protein, the polypeptide may be exposed to an immobilized reagent that binds to or modifies the polypeptide. Thus, the polypeptide may be subjected to affinity chromatography wherein an immobilized reagent that binds specifically to the polypeptide, such as an antibody, captures the antibody and impurities pass through the affinity chromatography column. The polypeptide can be subsequently eluted from the column by changing the conditions such that the polypeptide no longer binds to the immobilized reagent. The immobilized reagent may also be an enzyme such as a protease that modifies the polypeptide (Sahni et al., *Anal. Biochem.*, 193: 178–185 (1991) and Voyksner et al., *Anal. Biochem.*, 188: 72–81 (1990)).

Another type of purification process is filtration. Filtration of fine particle size contaminants from fluids has been accomplished by the use of various porous filter media through which a contaminated composition is passed such that the filter retains the contaminant. Retention of the contaminant may occur by mechanical straining or electrokinetic particle capture and adsorption. In mechanical straining, a particle is retained by physical entrapment when it attempts to pass through a pore smaller than itself. In the case of electrokinetic capture mechanisms, the particle collides with a surface within the porous filter and is retained on the surface by short-range attractive forces. To achieve electrokinetic capture, charge-modifying systems can be used to alter the surface charge characteristics of a filter (see, e.g., WO 90/11814). For example, where the contaminant to be removed is anionic, a cationic charge modifier can be used to alter the charge characteristics of the filter such that the contaminant is retained by the filter.

Monoclonal antibodies may be suitably separated from the precipitants by conventional antibody purification procedures such as, for example, gel filtration or electrophoresis, dialysis, HIC, affinity chromatography, e.g. protein-A SEPHAROSE™, protein-G, antigen-affinity or anti-IgG affinity chromatography, homogenization, clarification by filtration or centrifugation, precipitation, e.g. by treatment with ammonium sulfate, polyethylene glycol or caprylic acid, ion-exchange chromatography, e.g. using resins such as hydroxyapatite, e.g., resins containing calcium-phosphate such as ceramic-hydroxyapatite and BIOGEL HT™, and anion-exchange resins including those having a positively charged moiety (at neutral pH), such as diethylaminoethane (DEAE), polyethyleneimine (PEI), and quaternary aminoethane (QAE), for example, Q-SEPHAROSE FAST FLOW™ resin (Pharmacia), DEAE-SEPHAROSE FAST FLOW™ resin, DEAE-TOYOPEARL™ resin, QAE-TOYOPEARL™ resin, POROS-Q™ resin, FRACTOGEL-DMAE™ resin, FRACTOGEL EMD-TMAE™ resin, MATREX CELLUFINE DEAE™, and the like. Methods for isolating and purifying antibodies are further described in *Antibodies: A Laboratory Manual*"; Harlow and Lane, eds. (Cold Spring Harbor Laboratories, New York: 1988).

In one specific embodiment, the recovery step involves exposing the solubilized polypeptide to a solid phase to which is immobilized a reagent that binds to, or modifies, the polypeptide. In one embodiment, the solid phase is packed in a column and the immobilized reagent captures the polypeptide. In another embodiment, the reagent chemically and/or physically modifies the polypeptide and is immobilized on the solid phase that is, e.g., packed in a column, and the composition is passed through the column. For example, the polypeptide may comprise a precursor domain that the immobilized reagent removes as part of the recovery process, e.g., the precursor polypeptide is an antibody with a leucine zipper dimerization domain, which is removed by immobilized pepsin in the recovery process.

In this embodiment, the composition comprising the polypeptide and leached reagent (and optionally one or more further contaminants) is then passed through a filter bearing a charge that is opposite to the charge of the reagent at the pH of the composition, so as to remove leached reagent from the composition. The filter may be positively charged to remove contaminants that are negatively charged at the pH of the composition, such as acidic proteases, protein A, protein G or other reagents that can leach from affinity columns. Alternatively, the filter may be negatively charged to remove contaminants that are positively charged at the pH of the composition, such as basic proteases. Preferably, the charge characteristics of the polypeptide of interest in the composition passed through the filter are such that the polypeptide is not significantly retained by the filter and passes therethrough. The filter may be placed "in line" with the effluent treated as in the previous step (i.e., the effluent flows directly though the filter). This can be achieved by connecting the filter directly to the column effluent port, before the effluent is collected into a pool tank. The filter may be regenerated using techniques applicable to the type of filter used.

HIC has also been used for purifying antibody fragments. See, for example, Inouye et al., *Protein Engineering, pp.* 6, 8 and 1018–1019 (1993); Inouye et al., *Animal Cell Technology: Basic & Applied Aspects,* 5: 609–616 (1993); Inouye et al., *Journal of Biochemical and Biophysical Methods,* 26: 27–39 (1993); Morimoto et al., *Journal of Biochemical and Biophysical Methods,* 24: 107–117 (1992); and Rea et al., *Journal of Cell. Biochem.,* Suppl. 0, Abstract No. X1-206 (17 Part A), p. 50 (1993). HIC columns normally comprise a base matrix (e.g., cross-linked agarose or synthetic copolymer material) to which hydrophobic ligands (e.g., alkyl or aryl groups) are coupled. Many HIC columns are available commercially. Examples include, but are not limited to, Phenyl SEPHAROSE 6 FAST FLOW™ column with low or high substitution (Pharmacia LKB Biotechnology, AB, Sweden); Phenyl SEPHAROSE™ High Performance column (Pharmacia LKB Biotechnology, AB, Sweden); Octyl SEPHAROSE™ High Performance column (Pharmacia LKB Biotechnology, AB, Sweden); FRACTOGEL™ EMD Propyl or FRACTOGEL™ EMD Phenyl columns (E. Merck, Germany); MACRO-PREP™ Methyl or MACRO-PREP™ t-Butyl Supports (Bio-Rad, California); WP HI-Propyl (C 3)™ column (J. T. Baker, New Jersey); and TOYOPEARL™ ether, phenyl or butyl columns (TosoHaas, Pa.).

Examples of batch hydrophobic chromatography matrices are well known in the art and include $C_{18}$ alkyl chains linked to a support matrix such as SEPHAROSE™, agarose, or silica, e.g., butyl, phenyl, or octyl SEPHAROSE™, or polymers such as cellulose or polystyrene. U.S. Pat. No. 6,214,984 describes use of low-pH hydrophobic interaction chromatography (LPHIC) for antibody and antibody fragment purification. This method is particularly useful for purifying antibody fragments, especially correctly folded and disulfide linked antibody fragments (e.g., Fab fragments) from contaminating antibody fragments that are not correctly folded and/or disulfide linked. Prior to LPHIC, the antibody composition prepared from the cells is preferably subjected to at least one purification step, with examples including hydroxyapatite chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on certain human heavy chains (Lindmark et al., *J. Immunol. Meth.,* 62: 1–13 (1983)). Protein G is recommended for all mouse isotypes and for one human isotype (Guss et al., *EMBO J.,* 5: 1567–1575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the antibody comprises a CH 3 domain, the BAKERBOND ABX™ resin (J. T. Baker, Phillipsburg, N.J.) is useful for purification. Other techniques for protein purification such as fractionation on an ion-exchange column, ethanol precipitation, reverse-phase HPLC, chromatography on silica, chromatography on heparin SEPHAROSE™, chromatography on an anion- or cation-exchange resin (such as a polyaspartic acid column), chromatofocusing, SDS-PAGE, and ammonium sulfate precipitation are also available depending on the antibody to be recovered.

G. Uses of Polypeptides

The polypeptide thus recovered may be formulated in a pharmaceutically acceptable carrier and is used for various diagnostic, therapeutic, or other uses known for such molecules. For example, antibodies described herein can be used in immunoassays, such as enzyme immunoassays.

Therapeutic uses for the polypeptides purified using the method described herein are also contemplated. For example, a growth factor or hormone can be used to enhance growth as desired, and an antibody can be used for redirected cytotoxicity (e.g., to kill tumor cells), as a vaccine adjuvant, for delivering thrombolytic agents to clots, for delivering immunotoxins to tumor cells, for converting enzyme activated prodrugs at a target site (e.g., a tumor), for treating infectious diseases, or for targeting immune complexes to cell surface receptors.

Therapeutic formulations of the polypeptide are prepared for storage by mixing the polypeptide having the desired degree of purity with optional physiologically acceptable carriers, excipients, or stabilizers (*Remington's Pharmaceutical Sciences*, 16th edition, Osol, A., Ed., (1980)), in the form of lyophilized cake or aqueous solutions.

Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or polyethylene glycol (PEG).

The polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's *Pharmaceutical Sciences*, supra.

The polypeptide to be used for in vivo administration must be sterile. This is readily accomplished by filtration through sterile filtration membranes, prior to or following lyophilization and reconstitution. The antibody ordinarily will be stored in lyophilized form or in solution.

Therapeutic polypeptide compositions generally are placed into a container having a sterile access port, for example, an intravenous solution bag or vial having a stopper pierceable by a hypodermic injection needle.

The route of polypeptide administration is in accord with known methods, e.g., injection or infusion by intravenous, intraperitoneal, intracerebral, intramuscular, intraocular, intraarterial, or intralesional routes, or by sustained-release systems as noted below. The polypeptide is administered continuously by infusion or by bolus injection.

Suitable examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.*, 15: 167–277 (1981) and Langer, *Chem. Tech.*, 12: 98–105 (1982) or poly(vinylalcohol)), polylactides (U.S. Pat. No. 3,773,919, EP 58,481), copolymers of L-glutamic acid and gamma ethyl-L-glutamate (Sidman et al., *Biopolymers*, 22: 547–556 (1983)), non-degradable ethylene-vinyl acetate (Langer et al., supra), degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When, for example, encapsulated antibodies remain in the body for a long time, they may denature or aggregate as a result of exposure to moisture at 37° C., resulting in a loss of biological activity and possible changes in immunogenicity. Rational strategies can be devised for antibody stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release polypeptide compositions also include liposomally entrapped polypeptides. Liposomes containing the antibody are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 40304034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the most effective therapy with polypeptide.

An effective amount of polypeptide to be employed therapeutically will depend, for example, upon the therapeutic objectives, the route of administration, and the condition of the patient. Accordingly, it will be necessary for the therapist to titer the dosage and modify the route of administration as required to obtain the most beneficial therapeutic effect. A typical daily dosage might range from about 1 μg/kg to up to 10 mg/kg or more, depending on the factors mentioned above. Typically, the clinician will administer polypeptide until a dosage is reached that achieves the desired effect. The progress of this therapy is easily monitored by conventional assays.

The invention will be more fully understood by reference to the following examples. They should not, however, be construed as limiting the scope of the invention. All literature and patent citations herein are incorporated by reference.

EXAMPLE 1

Materials and Methods

A. Plasmids. Transformation, Fermentation
  1. Production of rhuFab'2 (xCD18)
    a. Plasmid Construction
  The control plasmid, pS1130, was designed for the dicistronic expression of anti-CD18 F(ab')$_2$ and it was based on the vector described by Carter et al., *Bio/Technology*, 10; 163–167 (1992). This design places transcription of the genes for both the light-chain and the heavy-chain fragments with a C-terminal leucine zipper under the control of a single phoA promoter. Transcription ends with a $\lambda t_0$ transcriptional terminator located downstream of the coding sequence for the heavy-chain-leucine zipper (Scholtissek and Grosse, *Nucleic Acids Res.*, 15(7): 3185 (1987)). The heat-stable enterotoxin II signal sequence (STII) precedes the coding sequence for each chain and directs the secretion of the polypeptide into the periplasm (Lee et al, *Infect. Immun.* 42: 264–268 (1983); Picken et al., *Infect. Immun.*, 42: 269–275 (1983)). Leucine zipper was attached to the C-terminal end of the heavy-chain fragment to promote the dimerization of the two Fab' arms.

The dual-promoter plasmid containing two separate translational units, pxCD18-7T3, temporally separates the transcription of light-chain from the transcription of heavy-chain sequences. As in pS1130, the light-chain sequence remains under the control of the phoA promoter. However, in pxCD18-7T3, a $\lambda t_0$ transcriptional terminator follows the light-chain coding sequence. Downstream of this terminator, the tacII promoter was added to control the transcription of the heavy-chain fragment/C-terminal leucine zipper (De-Boer et al., *Proc. Natl. Acad. Sci. USA*, 80: 21–25 (1983)). A second $\lambda t_0$ transcriptional terminator follows this coding sequence. Silent codon variants of the STII signal sequence were used to direct the secretion of both chains (Simmons and Yansura, *Nature Biotechnology*, 14: 629–634 (1996)).

A schematic comparison of the single promoter control plasmid vs. the dual-promoter plasmid is depicted in FIG. 1. The expression cassette sequence of pxCD18-7T3 is provided in FIG. 2 (SEQ ID NO: 1), and the amino acid sequences (SEQ ID NOS:2 and 3) from the two translational units are shown in FIGS. 3A (light chain) and 3B (heavy chain), respectively.

b. Fermentation

The host strain used in fermentation was a derivative of *E. coli* W3110, designated 59A7. The complete genotype of 59A7 is W3110 ΔfhuA phoAΔE15 Δ(argF-lac)169 deoC degP41 ilvG2096(Val<sup>r</sup>) Δprc sprW148R. The 59A7 host cells were transformed with the pxCD18-7T3 plasmid, and successful transformants were selected and grown in culture. An additional plasmid, pMS421, was co-transformed along with pxCD18-7T3. This additional plasmid, pMS421, is a pSC101-based plasmid which provides lacIq to improve control of the tacII promoter, and which also confers spectinomycin and strepromycin resistance.

For each 10-liter fermentation, a single vial containing 1.5 ml of culture in 10–15% DMSO was thawed into a 1-L shake flask containing 500 ml of LB medium supplemented with 0.5 ml of tetracycline solution (5 mg/ml) and 2.5 ml 1M sodium phosphate solution. This seed culture was grown for approximately 16 hours at 30° C. and was then used to inoculate a 10-liter fermentor.

The fermentor initially started with approximately 6.5 liters of medium containing about 4.4 g of glucose, 100 ml of 1M magnesium sulfate, 10 ml of a trace element solution (100 ml hydrochloric acid, 27 g ferric chloride hexahydrate, 8 g zinc sulfate heptahydrate, 7 g cobalt chloride hexahydrate, 7 g sodium molybdate dihydrate, 8 g cupric sulfate pentahydrate, 2 g boric acid, 5 g manganese sulfate monohydrate, in a final volume of 1 liter), 20 ml of a tetracycline solution (5 mg/ml in ethanol), 10 ml of FERMAX Adjuvant 27 (or some equivalent anti-foam), 1 bag of HCD salts (37.5 g ammonium sulfate, 19.5 g potassium phosphate dibasic, 9.75 g sodium phosphate monobasic dihydrate, 7.5 g sodium citrate dihydrate, 11.3 g potassium phosphate monobasic), and 200 g of NZ Amine A (a protein hydrolysate). Fermentations were performed at 30° C. with 10 slpm of air flow and were controlled at a pH of 7.0+0.2 (although occasional excursions beyond this range occurred in some cases). The back pressure of the fermentor and agitation rate was varied to manipulate the oxygen transfer rate in the fermentor, and, consequently, control the cellular respiration rate.

Following inoculation of the fermentor with the cell-containing medium from the shake flask, the culture was grown in the fermentor to high cell densities using a computer-based algorithm to feed a concentrated glucose solution to the fermentor. Ammonium hydroxide (58% solution) and sulfuric acid (24% solution) were also fed to the fermentor as needed to control pH. Further additions of anti-foam were also used in some cases to control foaming. When the culture reached a cell density of approximately 40 OD550, an additional 100 ml of 1M magnesium sulfate was added to the fermentor. Additionally, a concentrated salt feed (consisting of approximately 10 g ammonium sulfate, 26 g dibasic potassium phosphate, 13 g monobasic sodium phosphate dihydrate, 2 g sodium citrate dihydrate and 15 g monobasic potassium phosphate in 1 L of water) to the fermentor was started at a rate of 2.5 ml/mn when the culture reached approximately 20 OD550 and continued until approximately 1250 ml were added to the fermentation. Fermentations were typically continued for 72–80 hours.

During the fermentation, once the dissolved oxygen setpoint for the fermentation was reached, the concentrated glucose solution was fed based on the dissolved oxygen probe signal in order to control the dissolved oxygen concentration at the setpoint. Consequently, in this control scheme, manipulations of fermentor operating parameters such as the agitation rate or back pressure, which affect the oxygen transfer capacity in the fermentation, correspondingly manipulated the oxygen uptake rate or metabolic rate of the cells.

A mass spectrometer was used to monitor the composition of the off-gas from the fermentations and enabled the calculation of the oxygen uptake and carbon dioxide evolution rates in the fermentations.

When the culture reached a cell density of approximately 220 OD550, the agitation was decreased from an initial rate of 1000 rpm to approximately 725 rpm over approximately 12 hours. Fifty ml of 200 mM of isopropyl β-D-thiogalactopyranoside (IPTG) was added to induce heavy-chain synthesis approximately 12 hours after the culture reached a cell density of 220 OD550.

2. Production of Anti-Tissue Factor F(ab')$_2$ a. Plasmid Construction

A dual-promoter plasmid, pxTF7T3, was created similar to the dual-promoter plasmid pXCD18-7T3 set forth above, and used to enable temporal separation of anti-Tissue Factor light-chain and heavy-chain expression. The lacI sequence from the plasmid pMS421 was also incorporated onto pxTF7T3 to create a new dual-promoter plasmid pJVG3IL.

b. Fermentation

The host strain used in these fermentations was a derivative of *E. coli* W3110, designated 60H4. The complete genotype of 60H4 is: W3110 ΔfhuAΔmanA phoAΔE15 Δ(argF-lac)169 deoC2 degP41 ilvG2096(Val<sup>r</sup>) Δprc pre-suppressor. The 60H4 host cells were transformed with pJVG3IL and successful transformants were selected and grown in culture.

Fermentations were run under conditions similar to those for anti-CD18 F(ab'), as described above, with the principal exceptions that the run length varied between approximately 72 and 114 hours, and the heavy-chain sequence was induced using IPTG from approximately 4 to 12 hours following the attainment of a culture OD550 of 220.

3. Production of Full-Length Anti-TF Antibodies a. Plasmid Construction

The expression cassette for the plasmid pxTF-7T3FL comprises, from 5' to 3': (1) a phoA promoter (Kikuchi et al., *Nucleic Acids Res.*, 9(21): 5671–5678 (1981)); (2) trp Shine-Dalgarno (Yanofsky et al., *Nucleic Acids Res.*, 9: 6647–6668 (1981)); (3) a silent codon variant of the STII signal sequence (TIR relative strength about 7) (Simmons and Yansura, *Nature Biotechnology*, 14: 629–634 (1996)); (4) coding sequence for anti-tissue factor light chain; (5) $\lambda t_0$ terminator (Scholtissek and Grosse, *Nucleic Acids Res.*, 15: 3185 (1987)); (6) a tacII promoter ((DeBoer et. al., *Proc. Natl. Acad. Sci. USA*, 80: 21–25 (1983)); (7) a second trp Shine-Dalgarno; (8) a second silent codon variant of the STII signal sequence (TIR relative strength about 3); (9) coding sequence for anti-tissue factor full-length heavy chain; and (10) a second $\lambda t_0$ terminator. This expression cassette was cloned into the framework of the *E. coli* plasmid pBR322 (Sutcliffe, *Cold Spring Harbor Symp. Quant. Biol.*, 43: 77–90 (1978)).

Thus, the vector design of pxTF-7T3FL allows for the temporally separate expression of each chain by using two different, rather than two identical, promoters. In this plasmid, the light-chain sequence is under the control of the phoA promoter. However, the tacII promoter is used to control the transcription of the heavy-chain sequence. As is known in the art, phoA and tacII promoters are induced under substantially different conditions. A schematic comparison of a single-promoter plasmid paTF130 with pxTF-7T3FL is depicted in FIG. 4. The nucleic acid sequence of the expression cassette of pxTF-7T3FL (SEQ ID NO:4) is provided in FIG. 5, and the polypeptide sequences it encodes (SEQ ID NOS:5 and 6) are provided in FIGS. 6A (light chain) and 6B (heavy chain), respectively. The host cells below were co-transformed with pxTF-7T3FL and pJJ247. pJJ247 encodes a tacII promoter driving the expression of both DsbA and DsbC, with DsbA first in the series, and its construction is described in WO02/061090.

b. Fermentation

For small-scale expression *E. coli* strain 61 D6, with genotype W3110 ΔfhuA (ΔtonA) ptr3 laclq lacL8 ΔompTΔ (nmpc-fepE) degP41, was used as host cells. Following transformation, selected transformant picks were inoculated into 5 ml of Luria-Bertani medium supplemented with carbenicillin (50 µg/ml) and kanamycin (50 µg/ml) grown at 30° C. on a culture wheel overnight. A 10-liter fermentation was conducted using the media as described in WO02/061090 and the basic fermentation conditions were also as described in WO02/061090, except that the following modifications were made to the fermentation process: 300 mL of 1M $NaPO_4$, pH 7.0 was added at approximately 40 hours to give a concentration of about 30 mM. 100 nL of a 200-mM solution of IPTG was added at approximately 44 hours to give a concentration of about 2 mM. The fermentation was harvested 80 hours after inoculation.

B. Protein Identification

The one-dimensional SDS-PAGE gel electrophoresis was carried out in a 4–12% linear acrylamide gradient from Novex. Specifically, the system used was the NOVEX® NUPAGE™ System, consisting of NUPAGE™ Bis-TRIS Pre-Cast Gels (for low- to mid-molecular weight proteins).

C. Chemicals

The precipitation agent ethacridine lactate was 98% pure and purchased from Sigma (St. Louis, Mo., USA). Ethacridine lactate has a molecular weight of 361.4 Da. All other chemicals were of analytical grade.

D. Precipitation

The antibody- and F(ab')$_2$-containing *E. coli* materials were homogenized using a microfluidizer from Watts Fluidair Inc. (model B 12-04DJC, Kittery, Minn., USA). The cells were passed three times through the microfluidizer at 4-bar pressure. To avoid heat degradation of the proteins, the material was passed through an ice-water bath during each pass through the microfluidizer. The total protein concentration in the F(ab')$_2$ homogenates was 30 mg/ml. The full-length anti-TF homogenate, which was derived from re-suspended paste, had a total protein concentration of 18 mg/ml. The anti-TF paste was re-suspended in 25 mM TRIS-HCl buffer, pH 7.5.

The ethacridine lactate precipitation agent was dissolved in water to the desired final concentration (w/v).

1. pH study:

The precipitation experiments were performed with a constant ethacridine lactate concentration of 0.6% (w/v). A 0.8% ethacridine lactate solution was prepared and mixed with the *E. coli* homogenate in a 3:1 ratio, e.g., 3 ml of ethacridine lactate and 1 ml of *E. coli* homogenate. The pH was adjusted using HCl or NaOH depending on the pH desired.

2. Ethacridine Lactate Concentration Study:

The homogenate was diluted 4-fold with ethacridine lactate stock solutions (1:3 as in the pH study) and the pH was kept at a set value for each of the target proteins. For anti-CD18, the pH was 8.5 and for anti-TF pH 7.5. The final ethacridine lactate concentrations in the precipitation systems were 0.15, 0.30, 0.45, 0.60, 0.75, and 0.9% (w/v). As a reference a set of experiments with 0% ethacridine lactate was performed.

3. Conductivity/Dilution Study:

Various concentrations of NaCl were added to anti-CD18 homogenate to evaluate the effect of conductivity on protein precipitation. The NaCl concentrations studied were 0, 50, 100, 150, 200, and 400 mM. A reference series without ethacridine lactate was also performed to determine if any protein was precipitated due to the high salt concentration. The pH in this salt spike study was 8.5 and the anti-CD18 homogenate was diluted 4-fold. The ethacridine lactate concentration in the samples was 0.6% and 0% for the reference experiments.

To change the conductivity of the sample the homogenates were diluted in increasing amounts, and the pH was kept constant, pH 8.5 and 7.5 for anti-CD18 and anti-TF, respectively. All experiments had a final ethacridine lactate concentration of 0.6% (w/v). The homogenates were diluted 2, 3, 4, 5, 6, and 7-fold.

4. Temperature Study:

Some experiments were performed at elevated temperatures. The *E. coli* homogenate was diluted 4-fold and the final ethacridine lactate concentration was 0.6%. The pH was 8.5 or 7.5 for anti-CD18 and anti-TF, respectively. The samples were incubated in a thermostated water bath at a desired temperature, i.e., 50, 60, and 70° C. The samples were incubated for 20–120 minutes at elevated temperatures. One long-time incubation, 16 hours, was performed at 50° C.

After mixing the precipitation agent and *E. coli* homogenate together and adjustment of pH, the samples were incubated under agitating conditions for 30–60 minutes. The precipitation experiments were performed in glass tubes, at 4-ml scale. All experiments were performed in duplicate and average values were reported.

E. *E. coli* Protein Assay

Ethacridine lactate interacts with most commonly used protein measurement assays, e.g., Bradford, BCA, and spectrophotometric absorption measured at 280 nm. Thus, the total protein concentrations were measured using a generic *E. coli* protein ELISA. The samples were diluted in a fish gelatin-containing buffer (0.15 M NaCl, 0.1 M NaPO$_4$, 0.1% fish gelatin, 0.05% TWEEN 20™, 0.05% PROCLIN™ 300) to reduce the unspecified binding to the anti-*E. coli* protein antibodies. The coating antibody was Goat anti-Whole ECP. The conjugate antibody was an anti-antibody Whole ECP, attached to horseradish peroxidase. The absorption at 405 nm was monitored using a plate reader from Molecular Devices model SPECTRA MAX PLUS™ (Sunnyvale, Calif., USA).

F. Protein G Assay

To measure the recovered F(ab')$_2$ and antibody concentrations, a protein G affinity chromatography assay was used. An IMMUNO DETECTION™ protein G column was purchased from PerSeptive Biosystems (Framingham, Mass., USA). The column was equilibrated with phosphate-buffered saline (PBS) and eluted with PBS that had been pH adjusted to 2.2 with HCl. To minimize the interference from ethacridine lactate, samples were treated on exclusion spin columns (BIO-SPIN® 6 Tris columns (Bio-Rad Laboratories, Hercules, Calif., USA)) before assay. The spin columns were used as recommended by the vendor. A tetramethylammonium chloride (TMAC) wash step was introduced (Fahrner et al., *Biotechnology and Genetic Engineering Reviews*, 18: 302–327 (2001)) to the chromatography method to minimize any interference of residual ethacridine lactate in the sample. The assay was performed using a HPLC (HP1090™ liquid chromatograph) from Hewlett Packard (Mountain View, Calif., USA). The samples were diluted with PBS. Standard curves were prepared for each of the proteins using purified protein (from Genentech, Inc.).

G. DNA Assay

The DNA concentration in the supernatants after precipitation was measured using a Pico Green Kit from Molecular Probes (Eugene, Oreg., USA). It is a fluorescence assay where the fluorescent reagent (Pico green) binds to double-stranded DNA. The Pico green reagent is exited at 502 nm and the emission at 523 nm is recorded. The assay was performed using a fluorescence plate reader, SPECTRA MAX GENIN XS ™, from Molecular Devices (Sunnyvale, Calif., USA). Ethacridine lactate interacts with the Pico green assay and thus the precipitation agent was removed from the solution prior to analysis. Ethacridine lactate was removed from the sample using BIO-SPIN™ 6 TRIS columns, described in the protein G affinity chromatography assay section.

H. SDS-PAGE

Supernatents obtained after ethacridine lactate precipitation were analyzed by SDS-PAGE. Non-reduced 4–12% NUPAGE™ gels from Nova (San Diego, Calif., USA) were used to visualize the purification and recovery of anti-CD18 and anti-TF. Pre-cast gels were used and the running buffer was MOPS (pre-mnade concentrate purchased from Novex) The gels were stained with a filtered solution of COOMASSIE BRILLIANT BLUE R250™. The supernatants were volume compensated in regard to respective clarified *E. coli* extract. In this way, the intensity of the protein bands in the *E. coli* extract and samples should be identical if a 100% yield is obtained in the supernatarfls after precipitation with ethacridine lactate. Thus, the gels can be used to indicate accurately the extent of purification obtained from the precipitation.

I. Ethacridine Lactate Solubility

Two ethacridine lactate solutions, i.e., 0.6 and 1.2%, were studied. Each solution was divided into two aliquots and pH adjusted to 6.0 and 9.0, respectively. To obtain a slight buffer capacity in the system, the ethacridine lactate was dissolved in 10 mM Tris-HCl buffer. Each ethacridine lactate solution was exposed to increasing amounts of NaCl, i.e., 0, 50, 100, 150, 200, 300, and 600 mM. The samples were incubated for 3 hours, then centrifuged for 20 minutes at 12000 g in a microfuge (SORVALL MCI2V™, DuPont, Wilmington, Del., USA). The supernatants were assayed for ethacridine lactate by measuring the absorption at 270 nm. The spectrophotometer used was a HP8453 UV-VIS™ from Hewlett Packard (Wilmington, Del.), now Aligent Technologies (Palo Alto, Calif.) and known as the AGILENT 8453 UV-VIS™ spectrophotometer. A standard curve was derived from a solution with known ethacridine lactate concentration.

J. Turbidity

To measure the stability of supernatants as a function of time and temperature, the turbidity was monitored. The turbidity meter used was from HACH (model 2100N, Ames, Iowa, USA). The samples were measured at room temperature and without dilution of the sample.

The anti-CD18 homogenate was treated either with 0.6% ethacridine lactate, 0.2% PEI, or only water. In all of the three samples the anti-CD18 homogenate was diluted 4-fold and the pH was 7.2±0.2. After centrifugation for one hour at 4000 g the supernatants were recovered and divided into two aliquots. One part of each sample was incubated at room temperature (21° C.) and the other one at 4° C.

Results and Discussion

Effect of pH

The ethacridine lactate molecule is positively charged over most of the pH interval (Miller, supra; Neurath and Brunner, supra; Franek, *Methods in Enzymology*, ed. Langone, J. J., Van Vunakis, H., 121: 631–638 (1986)). However, since pH changes affect the charge on polypeptides and there is a correlation between the pI of the polypeptide and the pH at which it precipitates when exposed to ethacridine lactate (Neurath and Brunner, supra), the effect of pH on degree of purification in the method of this invention was investigated.

Figure 8:
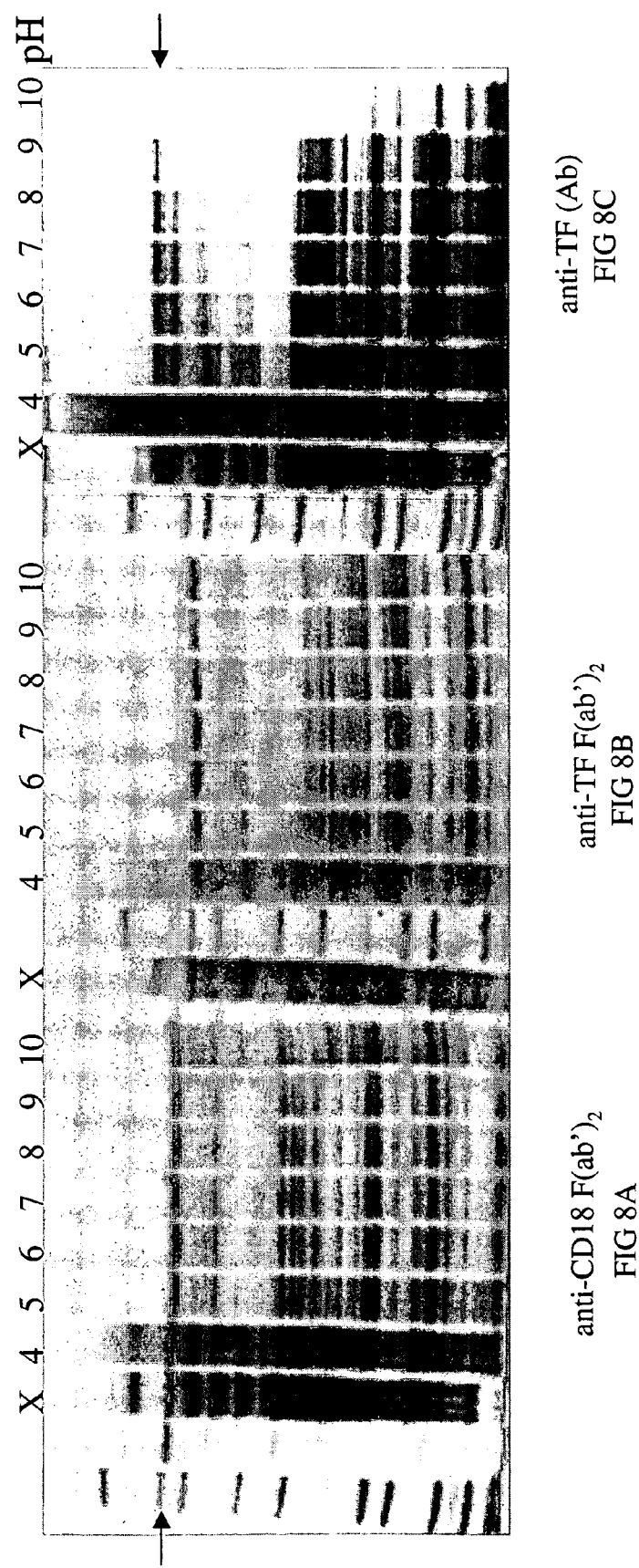
FIGS. 8A–8C show a non-reduced SDS-PAGE Coomassie-blue-stained gel analysis of three supernatants after precipitation with ethacridine lactate. The precipitation was performed at different pH values, as indicated at each lane. The lanes indicated with an X are the clarified supernatant of the respective *E. coli* homogenate, i.e., anti-CD18 F(ab')$_2$, anti-TF F(ab')$_2$, and full-length anti-TF (FIGS. 8A, 8B, and 8C, respectively). The homogenates were diluted 4-fold with a 0.8% ethacridine lactate solution, i.e., a final concentration of 0.6% ethacridine lactate in each experiment. All samples were volume compensated before loading on to the gel. Hence, the intensity of the bands should be comparable to the extract (X) if a 100% recovery is obtained. The arrows indicate product band.

Homogenates containing anti-CD18 F(ab')$_2$, anti-TF F(ab')$_2$, and full-length anti-TF, respectively, were exposed to a 0.6% ethacridine lactate solution adjusted to cover the pH range 4–10. FIGS. 8A–8C show the clarified phases after ethacridine lactate treatment and centrifugation of each of these proteins, respectively.

In Table 1, anti-TF was studied both as a full-length antibody and as a F(ab')$_2$. *E. coli* homogenates were treated at a 1:3 ratio with a 0.8% (w/v) ethacridine lactate solution, i.e., a final ethacridine lactate concentration of 0.6% in the sample. The pH was adjusted with HCl and NaOH respectively to obtain desired pH. The yields and purification factors are calculated in respect to each of the clarified cell homogenates. The DNA concentration in the recovered supernatants is also reported in the table.

TABLE 1

The pH effect on the purification and yield of αCD18 and αTF
when treated with ethacridine lactate

| pH | anti-CD18 F(ab')$_2$ Purification factor* | Yield (%) | anti-TF F(ab')$_2$ Purification factor* | Yield (%) | anti-TF full-length Ab Purification Factor* | Yield (%) | DNA conc. (µg/ml) |
|---|---|---|---|---|---|---|---|
| 4  | 3.2 | 100 | 1.8 | 93 | 2.4 | 100 | 0.2 |
| 5  | 5.3 | 100 | 5.1 | 93 | 4.4 | 100 | 0.1 |
| 6  | 5.6 | 100 | 5.1 | 67 | 6.7 | 100 | ≦0.001 |
| 7  | 5.6 | 100 | 5.4 | 70 | 7.1 | 86  | ≦0.001 |
| 8  | 5.6 | 87  | 5.0 | 42 | 6.2 | 65  | ≦0.001 |
| 9  | 5.4 | 84  | 4.7 | 22 | 5.3 | 24  | ≦0.001 |
| 10 | 4.2 | 85  | 4.7 | 18 | 0.9 | 7   | 0.3 |

*A value of 1 is the same purification as is obtained in the system not treated with ethacridine lactate.

It can be seen that for all three proteins a bell-shaped curve was obtained with respect to extent of purification and DNA concentration over the pH range of 4 to 10. At the middle pH values, i.e., pH 5–9, an approximately 5-fold purification was obtained. The yield of anti-CD18 F(ab')$_2$ and anti-TF antibody full-length and F(ab')$_2$ decreased with higher pH, and anti-TF antibody full-length and F(ab')$_2$ had a stronger pH dependence than anti-CD18 F(ab')$_2$. The yield of anti-CD18 F(ab')$_2$ is decreased from 100 to 85% and of anti-TF F(ab')$_2$ from 93 to 18% in the pH range 4–10. Without being limited to any one theory, this could partly be due to the lower pI of anti-TF compared to anti-CD18, e.g., pI7.5 and 8.9, respectively; however, these are theoretically calculated pI values.

The full-length anti-TF protein has an even stronger pH dependence than the F(ab')$_2$ version of the protein. The purity of full-length anti-TF is highest at pH 7.0. At pH above 8 significant yield losses are observed (FIG. 8C). For the full-length anti-TF a pH of about 7.0 is preferred, i.e., a 7.1-fold purification and 86% yield. One possible explanation for the higher losses of anti-TF compared to anti-CD18, without being limited to any one theory, is that anti-TF has more negative surface charges than anti-CD18 when incubated above its pI. Analogous to this, without being limited to any one theory, the larger full-length anti-TF might have more negative surface charges than the corresponding F(ab')$_2$ and thus a significantly higher yield loss is observed when increasing the pH.

However, components other than cell debris and host protein have to be removed from the target polypeptide. One such component is DNA. The major disadvantage of having high DNA concentration together with the target polypeptide is that the viscosity of the solution increases. This will have a negative impact on the further downstream processing. In addition, if an anion-exchange column is used as the first capture column, the negatively charged DNA will bind to the resin and thus reduce the protein capacity of the column.

Hence, the DNA concentration in the supernatants after precipitation with ethacridine lactate was determined. The results show that the DNA concentration in the supernatants after ethacridine lactate precipitation is significantly reduced compared to the initial DNA concentration obtained in the *E. coli* homogenate. However, the DNA concentration in the supernatant increased as the pH thereof decreased, i.e., 0.1 and 0.2 µg/ml at pH 5.0 and 4.0 respectively. Without being limited to any one theory, this could be due to the fact that the phosphates on the DNA become less negatively charged at lower pH. At very high pH, e.g., pH 10.0, the DNA concentration is significantly increased (0.3 µg/ml) and the protein purity also was decreased. Without limitation to any one theory, this is partly due to the fact that the pH is above the pI of the antibody and F(ab')$_2$; however, it can also partly be due to the fact that ethacridine lactate is less charged at this pH.

Effect of Ethacridine Lactate Concentration

The *E. coli* homogenates were mixed with ethacridine lactate solutions in a (1:3) ratio. The ethacridine lactate concentration in the samples was increased in 0.15% increments from 0 to 0.9% (w/v). This study was performed at pH 8.5, 7.5, and 6.0 for anti-CD18, anti-TF F(ab')$_2$, and full-length antibody, respectively.

Table 2 shows the effect of ethacridine lactate concentration on purification and yield. In Table 2, anti-TF was studied both as a full-length antibody and as a F(ab')$_2$. *E. coli* homogenates were treated at a 1:3 ratio with different concentrations of ethacridine lactate solutions; the final ethacridine lactate concentration in the sample is reported. The pH of the anti-CD18, anti-TF(F(ab')$_2$), and full-length anti-TF was 8.5, 7.5 and 6.0, respectively. The DNA concentration in the recovered supernatants is also reported in the table.

TABLE 2

The effect on purity and yield of anti-CD18 and anti-TF when treated with increasing ethacridine lactate concentration

| Ethacridine lactate (% w/v) | anti-CD18 F(ab')$_2$ | | anti-TF F(ab')$_2$ | | anti-TF Full-length Ab | | DNA conc. (µg/ml) |
|---|---|---|---|---|---|---|---|
| | Purification factor* | Yield (%) | Purification factor* | Yield (%) | Purification Factor* | Yield (%) | |
| 0 | 1.0 | 100 | 1.0 | 100 | 1.0 | 100 | 77.9 |
| 0.15 | 1.1 | 100 | 1.3 | 97 | 3.4 | 100 | 3.9 |
| 0.30 | 1.7 | 100 | 2.2 | 93 | 6.7 | 100 | 0.4 |
| 0.45 | 4.0 | 100 | 5.2 | 96 | 6.5 | 100 | 0.2 |
| 0.60 | 5.8 | 100 | 5.6 | 98 | 6.5 | 100 | ≦0.001 |
| 0.75 | 5.9 | 100 | 5.6 | 78 | 6.3 | 100 | ≦0.001 |
| 0.90 | 5.9 | 100 | 5.4 | 70 | 6.3 | 100 | ≦0.001 |

*A value of 1 is the same purification as is obtained in the system not treated with ethacridine lactate.

Figures 9, 9A, 9B, 9C:
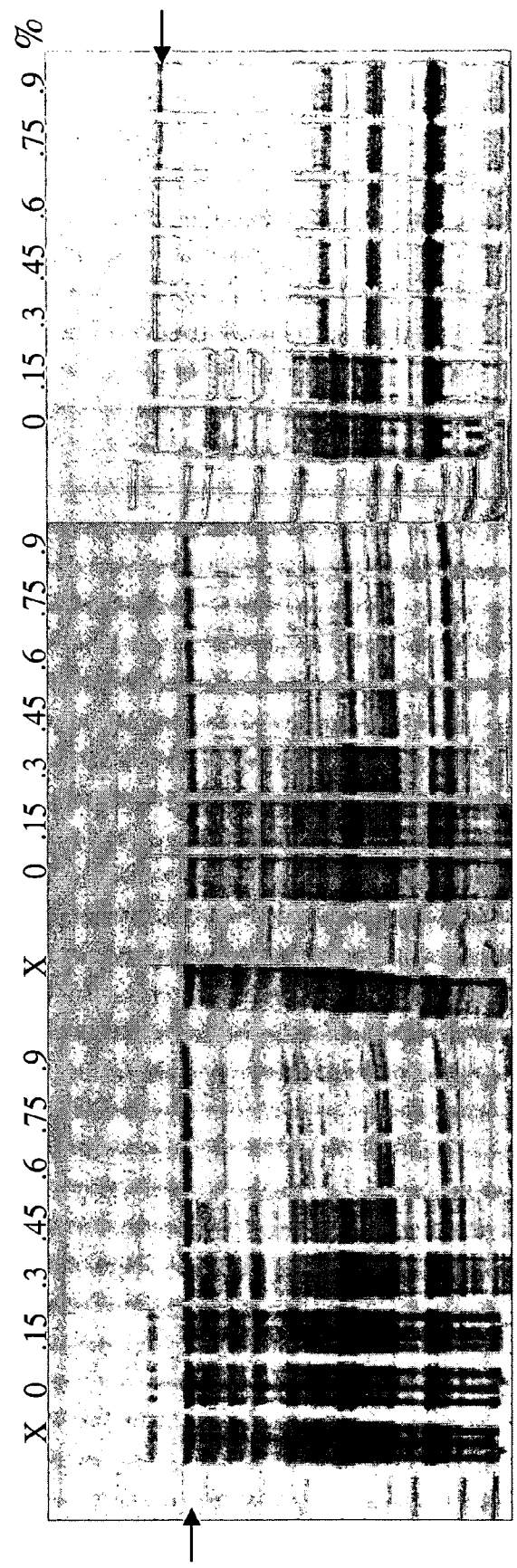
FIGS. 9A–9C show a non-reduced SDS-PAGE Coomassie-blue-stained gel analysis of supernatants after precipitation with ethacridine lactate. The precipitation was performed with different ethacridine lactate concentrations, as indicated at each lane. The lanes indicated with an X are the clarified supernatant of the respective *E. coli* homogenate, i.e., anti-CD18F(ab')$_2$, anti-TF F(ab')$_2$, and full-length anti-TF (FIGS. 9A, 9B, and 9C, respectively). The pH of the anti-CD18 F(ab')$_2$, anti-TF F(ab')$_2$, and full-length anti-TF was 8.5, 7.5, and 6.0, respectively. The conductivity in the samples was 3.2±0.2 mS/cm. All samples were volume compensated before loading on to the gel. Hence, the intensity of the bands should be comparable to the extract (X) if a 100% recovery is obtained. The arrows indicate product band.

The purity of the antibodies was shown to be strongly correlated with the concentration of ethacridine lactate (FIGS. 9A–9C and Table 2). At ethacridine lactate concentrations above about 0.6% the effect of increased ethacridine lactate concentration on increased purification was not dramatic. However, at lower concentrations of ethacridine lactate, i.e. when ethacridine lactate is deficient, every slight addition of the precipitation agent resulted in a substantial additional purification of the F(ab')$_2$.

The yield of anti-CD18 F(ab')$_2$ was not affected by the addition of different concentrations of ethacridine lactate. The step recovery for both of the F(ab')$_2$ was about 90% for all the experiments. However, it appears easier to obtain quantitative recovery of the F(ab')$_2$ anti-CD18 than the anti-TF F(ab')$_2$. Without being limited to any one theory, this could be because there are more negative surface charges on the anti-TF F(ab')$_2$ compared to the anti-CD18 F(ab')$_2$ at the pH studied. The full-length anti-TF reached its maximum purification at a lower ethacridine lactate concentration than the corresponding F(ab')$_2$ protein, 0.3% and 0.6%, respectively. Without being limited to any one theory, this is probably due to a lower overall protein concentration in the anti-TF full-length homogenate, i.e., 18 and 30 mg/ml for the full-length and F(ab')$_2$ anti-TF, respectively. The full-length anti-TF is also derived from re-suspended paste and the F(ab')$_2$ is taken as broth directly from the fermentor. Hence, soluble culture media components present in the E. coli broth will not be present in the re-suspended full-length anti-TF material, which could partly explain the differences seen, without limitation to any one theory.

The DNA concentration in the supernatants is strongly correlated with the data obtained for the protein purification. At 0.6% or higher ethacridine lactate addition, no DNA was detected in the supernatants. There is also a clear trend of decreasing DNA concentration, i.e., 78 to 0 µg/ml, in the supernatants when the ethacridine lactate concentration is increased from 0 to 0.6%.

Effect of Conductivity

As ethacridine lactate precipitates proteins partly due to the charged characteristics of the molecule (Neurath and Brunner, supra), the conductivity of the sample may have an effect on the purity of the antibody and F(ab')$_2$ after precipitation. Hence, if the sample has high salt concentration, i.e., high conductivity, the salts could shield the proteins from the ethacridine lactate and thus reduce the purification effect.

Figure 10:
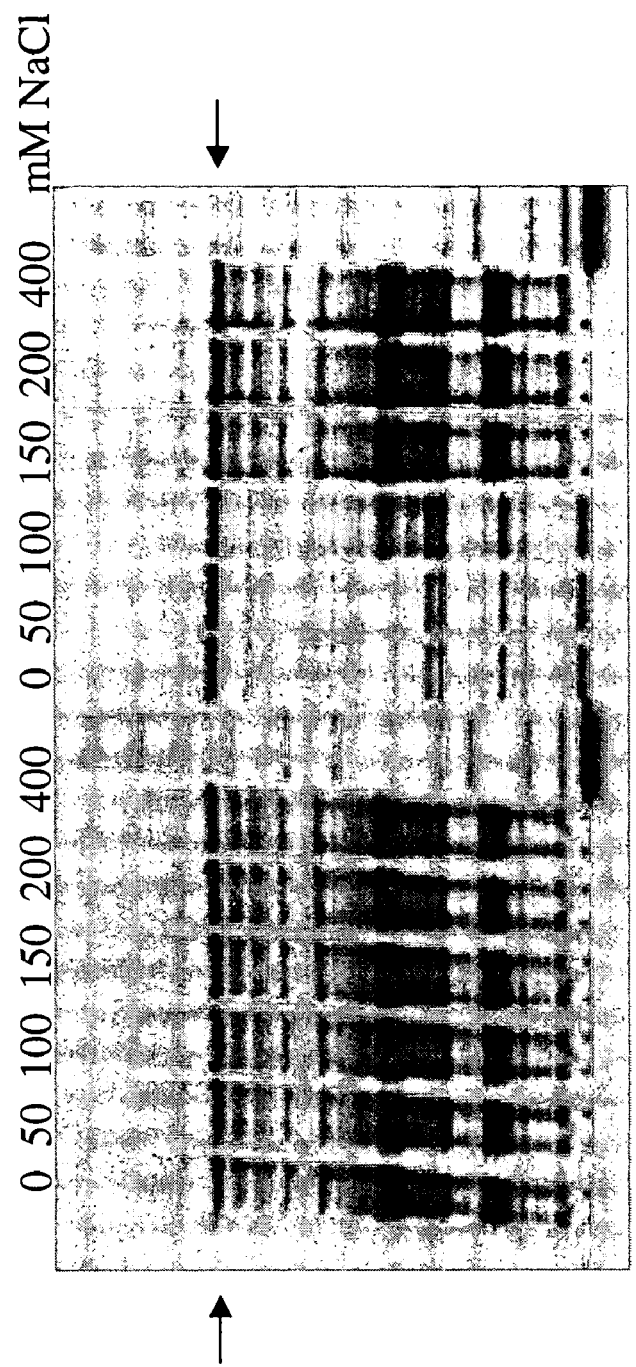
FIGS. 10A and 10B show a non-reduced SDS-PAGE Coomassie-blue-stained gel analysis of two supernatants after dilution with water or with ethacridine lactate, respectively. The precipitation was performed at different conductivity levels. *E. coli* homogenate containing anti-CD18 F(ab')$_2$ was used for this study. The homogenate was diluted 4-fold with either water (FIG. 10A) or a 0.8% ethacridine lactate solution, i.e., a final ethacridine lactate concentration of 0.6% in each experiment (FIG. 10B), and the pH was adjusted to 8.3. To alter the conductivity, NaCl was added to the samples in different concentrations of 0–400 mM (as indicated in the figures). The arrows indicate product band.

Anti-CD18 homogenate was subjected to two sets of experiments to separate the effect of the conductivity from the protein concentration in the sample. To both sets of experiments NaCl was added (0–400 mM). One set of the experiments contained 0.6% ethacridine lactate and in the other set water was used. The water-containing systems were used as controls, so that if the NaCl would give rise to any precipitation this could be distinguished from the precipitation derived from the ethacridine lactate. In the systems without ethacridine lactate, i.e. the water systems, no protein precipitation was observed in the 0–400 mM NaCl concentration range (FIG. 10A). The ethacridine lactate-containing experiments showed a strong increase in the purification of anti-CD18 when the conductivity was decreased (FIG. 10B).

Without being limited to any one theory, one reason for the improved purification of anti-CD18 at lower conductivity could be the low shielding capacity of the charged ethacridine lactate at low salt concentration. Analogous shielding effects have been seen when PEI is used for protein purification at increasing salt concentration (Jendrisak, supra). However, an even more important factor is the low solubility of ethacridine lactate at higher salt concentrations (Miller, supra; Neurath and Brunner, supra; Franek, supra). At 100 mM NaCl precipitation of ethacridine lactate was observed in the extraction system, and as the salt concentration was increased, more of the ethacridine lactate was precipitated. Hence, less ethacridine lactate is soluble in the system and available to precipitate proteins and other biomolecules.

Figure 11:
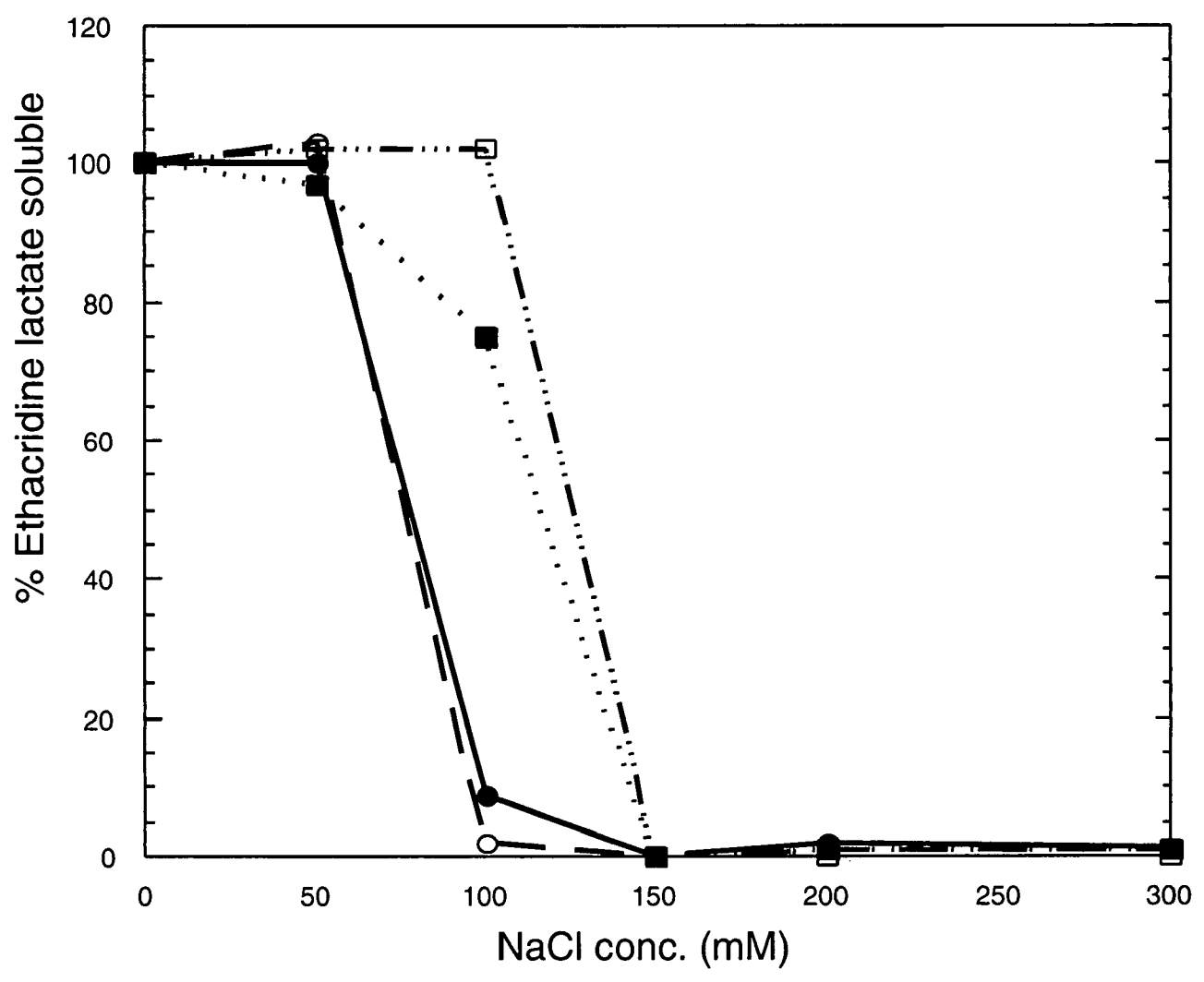

When the solubility of ethacridine lactate as a function of NaCl concentration was studied, a pH dependence was observed (FIG. 11). At pH 6 no significant difference in the solubility between the 0.6 and 1.2% ethacridine lactate solution was observed. Both solutions were soluble at 50 mM NaCl but nearly fully precipitated at 100 mM. For the pH 9 solutions, where the ethacridine lactate was less charged, a significant difference in solubility was seen between the two concentrations of ethacridine lactate. The 0.6% ethacridine lactate solution precipitated at lower salt concentration than the more concentrated ethacridine lactate solution (FIG. 11). Chlorides have been shown to precipitate ethacridine lactate especially efficiently (Franek, supra).

In practice, the conductivity of a precipitation experiment will be determined by the dilution factor. Hence, a set of experiments was performed where the impact of the dilution factor of the *E. coli* homogenate was studied. The overall ethacridine lactate concentration was kept constant, i.e., 0.6% (w/v), but the conductivity of the sample was decreased with increased dilution. The results are shown in Table 3. In Table 3, anti-TF was studied both as a full-length antibody and as a F(ab')$_2$. The concentration of ethacridine lactate in each experiment was 0.6% (w/v). The pH of the anti-CD18, anti-TF(F(ab')$_2$), and full-length anti-TF was 8.5, 7.5 and 6.0, respectively. The yields and purification factors are calculated in respect to each of the clarified cell homogenates. The DNA concentration in the recovered supernatants is also reported in the table.

dine lactate to protein and DNA increases with the higher dilutions, i.e., at lower conductivity. Thus, the effect seen in this example is both of lowering conductivity and of increasing amounts of ethacridine lactate.

Effect of Temperature

Temperature is a factor that is known to be important when performing precipitation experiments. Thus, some elevated temperatures were studied in combination with ethacridine lactate. The effect of incubation time at elevated temperature was also investigated.

TABLE 3

The effect on the purity and yield of anti-CD18 and anti-TF upon dilution of the *E. coli* homogenates in different amounts

| Dilution (times) | Cond. (mS) | anti-CD18 F(ab')$_2$ | | anti-TF F(ab')$_2$ | | anti-TF Full-length Ab | | DNA conc. (µg/ml) |
|---|---|---|---|---|---|---|---|---|
| | | Purification factor* | Yield (%) | Purification factor* | Yield (%) | Purification Factor* | Yield (%) | |
| 2 | 5.0 | 2.4 | 72 | 2.3 | 77 | 3.4 | 70 | 20.7 |
| 3 | 4.0 | 4.1 | 76 | 4.0 | 60 | 6.7 | 82 | 0.5 |
| 4 | 3.2 | 5.5 | 71 | 4.9 | 95 | 6.7 | 95 | ≦0.001 |
| 5 | 2.7 | 6.1 | 88 | 5.2 | 100 | 6.5 | 100 | ≦0.001 |
| 6 | 2.4 | 6.1 | 92 | 5.0 | 100 | 6.0 | 100 | ≦0.001 |
| 7 | 2.1 | 6.3 | 100 | 5.1 | 100 | 6.0 | 100 | ≦0.001 |

*A value of 1 is the same purification as is obtained in the system not treated with ethacridine lactate.

The results showed that the purification of F(ab')$_2$ was enhanced if the conductivity was lowered by increasing dilution. However, at a conductivity of 3.5 mS or lower the effect of conductivity was minor. For the *E. coli* homogenate used in this Example a 4-fold dilution had to be performed to obtain conductivity below 3.5 mS. For the full-length anti-TF antibody a slightly lower dilution can be performed than for the F(ab')$_2$ homogenates. Without limitation to any one theory, this can be due to the fact that the protein concentration in the full-length homogenate is lower. Furthermore, as the full-length material is derived from re-suspended paste, some of the media components that might affect the precipitation have been removed prior to the ethacridine lactate precipitation.

In these experiments the protein concentration was decreased with increased dilution (lowering of the conductivity). Thus, even if 0.6% ethacridine lactate, which was found to be an excess concentration in the ethacridine lactate concentration study, was added, maximum removal of host protein and DNA was not obtained in the less diluted sample. This is due to the increased homogenate concentration, i.e., overall protein and DNA, in these samples compared to the sample performed in the ethacridine lactate concentration study. Hence, the overall concentration of protein, DNA, and other components will affect the ethacridine lactate concentration or alternatively the dilution required. The yield of anti-CD18 F(ab')$_2$ and full-length and F(ab')$_2$ anti-TF increased with the decrease in conductivity.

Figure 12:
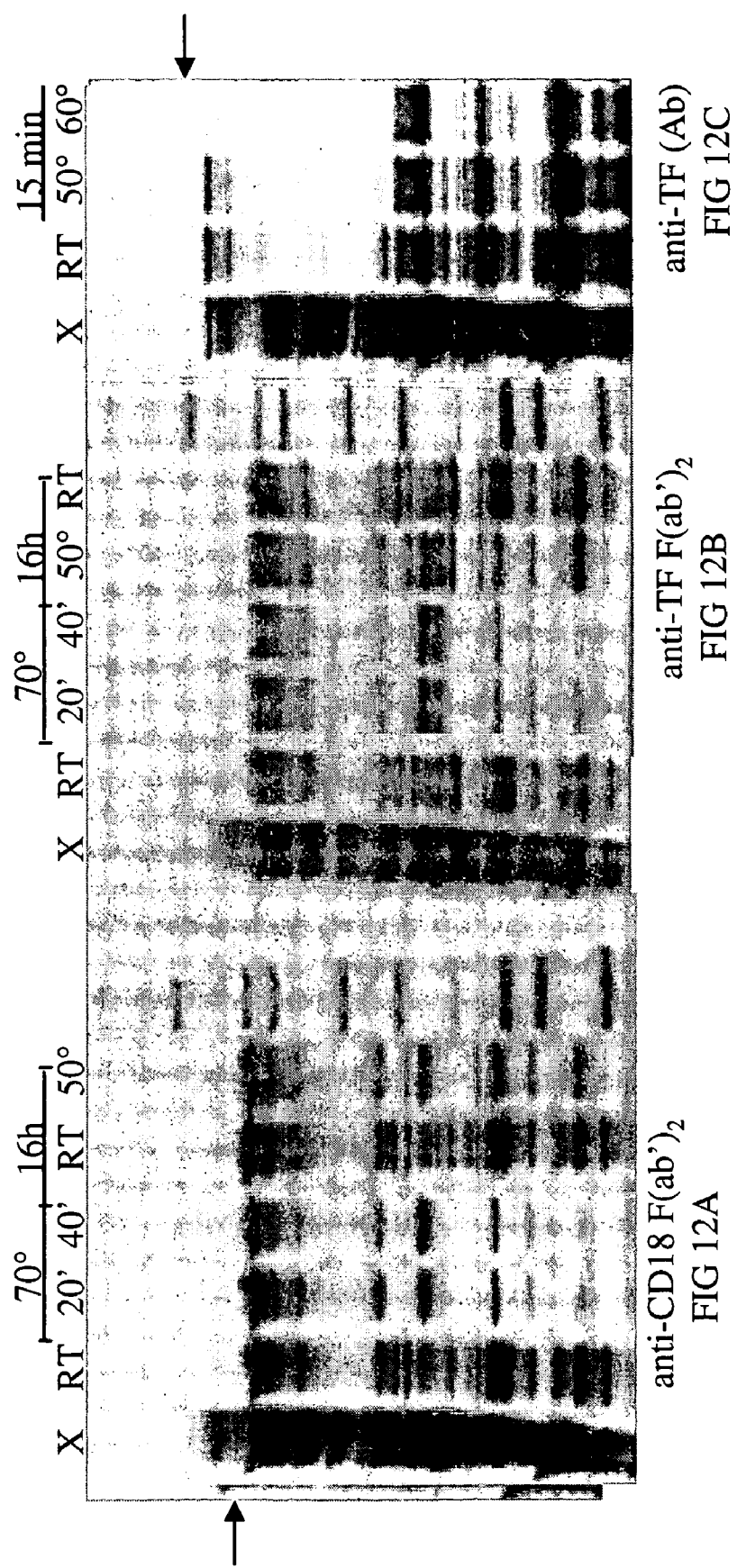
FIGS. 12A–12C show a non-reduced SDS-PAGE Coomassie-blue-stained gel analysis of three supernatants after precipitation with ethacridine lactate. The precipitation was performed at elevated temperatures. The lanes indicated with an X are the clarified supernatant of the respective *E. coli* homogenate, i.e., anti-CD18 (F(ab')$_2$), anti-TF (F(ab')$_2$), and full-length anti-TF (FIGS. 12A, 12B, and 12C, respectively). The homogenate was diluted 4-fold to a final ethacridine lactate concentration of 0.6% and the pH was adjusted to 8.5, 7.5, and 6.0 for anti-CD18 (F(ab')$_2$), anti-TF (F(ab')$_2$), an full-length anti-TF, respectively. The temperature and time for incubation are indicated in the figures. The arrows indicate product band.

The effect on the DNA removal was also found to be conductivity dependent. At a two-fold dilution, i.e., 5.0 mS, a high DNA concentration was obtained in the supernatant, 20.7 µg/ml. However, if a 3-fold dilution was performed, i.e., 4.0 mS, the concentration was decreased to 0.5 µg/ml, and at even higher dilution no DNA was detected. As pointed out earlier, in this case the total amount of ethacri- Incubation at elevated temperature, i.e., 50–70° C., had a positive effect on the purity of the two F(ab')$_2$ proteins (FIGS. 12A and 12B). The higher the temperature, the more efficient the purification. An incubation at 70° C. significantly improved the purity of the F(ab')$_2$ proteins. Incubating the sample for longer time, i.e., 40 min compared to 20 min, at 70° C. did not improve the purity of the F(ab')$_2$ (FIGS. 12A and 12B), but an approximately 10% loss in yield was observed. However, when the sample was incubated above 70° C., no F(ab')$_2$ was recovered, which is due to temperature precipitation of F(ab')$_2$ as well as other *E. coli* proteins.

To investigate the effect of the incubation time more closely, an experiment was performed where the samples were incubated for 16 h and 30 min at 50° C. The results showed that there was no significant purification improvement for the sample that had been incubated for 16 h compared to 30 min at this temperature. This indicates that temperature precipitation is a rapid phenomenon, which suggests that a fast heating to appropriate temperature would be more suitable then a long incubation time.

The full-length anti-TF was also studied at elevated temperatures. A 15-min incubation at 50° C. had a slightly positive effect on the purity of the antibody and no losses in recovered material were observed compared to a sample incubated at room temperature (FIG. 12C). However, if the temperature was increased to 60° C., nearly all anti-TF precipitated. The data indicate that the full-length anti-TF has lower stability at elevated temperature than the F(ab')$_2$ anti-TF protein.

Since an increase in temperature could give rise to modifications of the target polypeptide, the stability of the particular polypeptide of interest at elevated temperature would need to be evaluated before implementation.

Stability of Feed Stream

It is important to recover the cleanest feed streams possible. However, another important characteristic of the feed stream is its stability over time. Hence, the stability of supernatants after ethacridine lactate or PEI treatment and a supernatant after plain centrifugation was compared. Each of the supernatants was incubated at two temperatures, i.e., room temperature (21° C.) and 4° C. The stability was monitored by measuring the turbidity of the respective sample.

Figure 13:
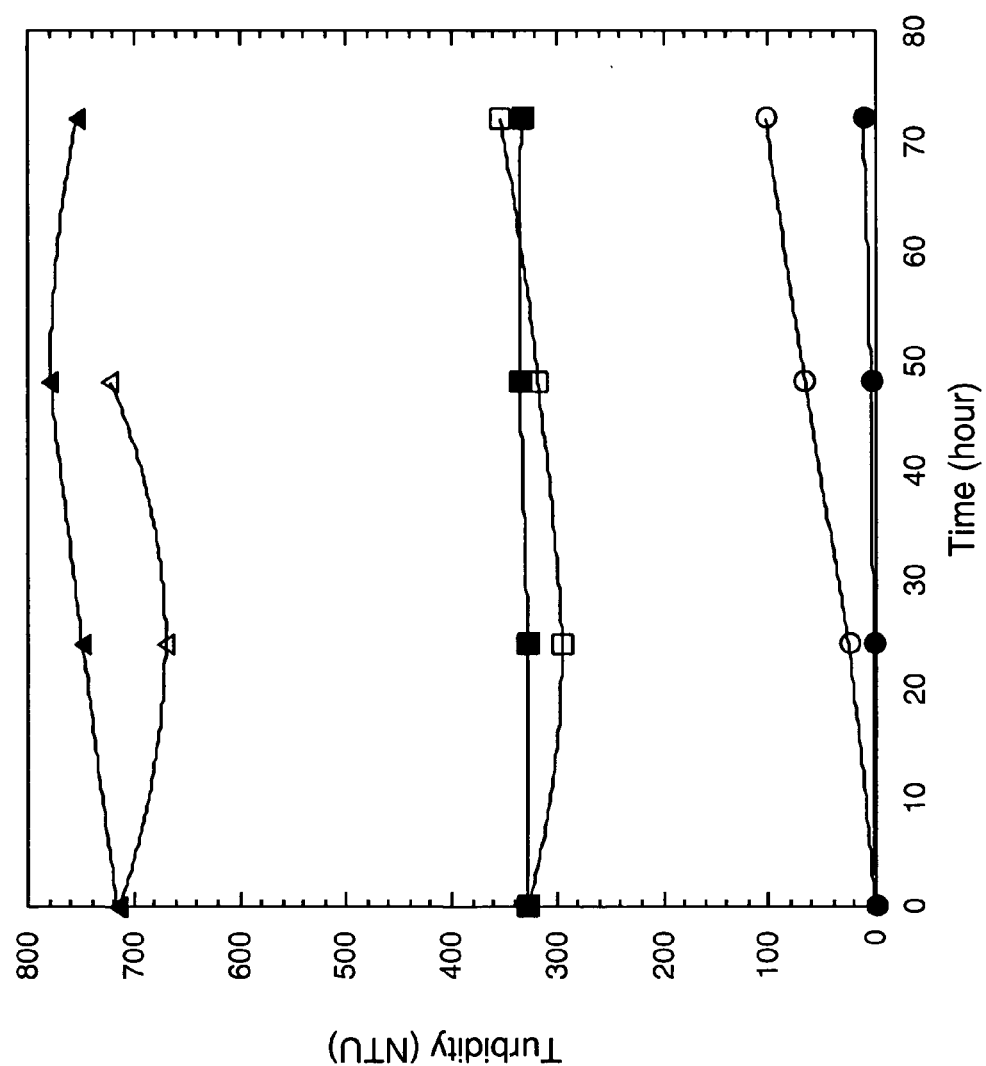
FIG. 13 shows a graph of turbidity as a function of time for three different supernatants. Supernatants from anti-CD18 homogenate treated with 0.6% ethacridine lactate are symbolized by solid circles (4° C.) or open circles (21° C.), and 0.2% PEI-treated sample is shown as solid squares (4° C.) and open squares (21° C.). A supernatant recovered from a clarified anti-CD18 homogenate that had been diluted with water before concentration is shown as solid triangles (4° C.) and open triangles (21° C.). In all cases the anti-CD18 homogenate had been diluted 4-fold and the pH was 7.2.

In FIG. 13 the change in turbidity over time is shown for the three different supernatants, i.e., ethacridine lactate, PEI, and non-treated clarified supernatant, respectively. It can clearly be seen that the polyelectrolytes, i.e., ethacridine lactate and PEI, significantly reduced the turbidity of the supernatant. Directly after clarification the non-treated clarified supernatant had a turbidity of about 700 NTU, whereas the PEI-treated sample only had half that turbidity, i.e., 327 NTU, and the ethacridine lactate supernatant had a turbidity of 1 NTU. There was not a major difference seen, either over time or with incubation temperatures, when monitoring the turbidity of the PEI-treated supernatant. For the supernatant that had only been centrifuged there was a trend of lower turbidity in the room temperature sample during the first 48 hours. However, the room temperature sample at 72 hours could not be measured due to high turbidity of the sample. The ethacridine lactate-treated supernatant had very low turbidity that was not significantly increased if incubated at 4° C. When the sample was incubated at 21° C. the turbidity increased significantly, i.e., from 1 to 100 NTU over 72 hours. However, 100 NTU is still less than the turbidity obtained for the other two supernatants directly after clarification. Hence, it can be concluded that the supernatant recovered after ethacridine lactate treatment at pH 7 is a stable feed stream.

CONCLUSION

Ethacridine lactate can successfully be used as precipitation agent for the primary recovery of heterologous polypeptides from culture broth or homogenate. When ethacridine lactate is used as precipitation agent, the ideal target polypeptide preferably has a higher pI than the average host proteins. Hence, most proteins can be negatively charged and become precipitated by ethacridine lactate at the same time as the target protein is positively charged and thus recovered in the supernatant.

The preferred concentration of ethacridine lactate for precipitation is highly dependent on the concentration of host protein and DNA in the broth or homogenate. The higher the protein and DNA concentration in the broth or homogenate, the higher is the amount of ethacridine lactate required. Hence, the more negatively charged components available for ethacridine lactate to complex with, and thus precipitate, the higher is the preferred amount of ethacridine lactate for precipitation. The lower the conductivity of the solution when performing the precipitation, the more efficient is the purification of the polypeptide. The precipitation step will give significant polypeptide purification and DNA reduction at the same time as cell debris is removed.

For efficient host protein and DNA precipitation, the pH is generally between about 4 and 10, and preferably no more than about pH 9, as the molecule becomes less charged above this pH. Ethacridine lactate should more preferably be used in the about pH 5–9 range when purifying polypepride. To improve the purification, a short incubation at elevated temperature can be performed. However, stability at elevated temperatures has to be determined for the particular polypeptide of interest to avoid precipitation of the target polypeptide. Also the quality of the recovered target polypepride has to be investigated to confirm that no modifications of the target polypeptide take place.

What is claimed is:

1. A method for purifying a desired heterologous polypeptide from microbial fermentation broth or homogenate in which it is produced and solubilized comprising adding to the broth or homogenate an effective amount of a solution of ethacridine lactate to precipitate host cell impurities under conditions wherein the majority of the polypeptide remains soluble, and separating the desired polypeptide from the broth or homogenate, wherein the temperature of the broth or homogenate after addition of the ethacridine lactate is from about 50 to 65° C. held for about 1–60 minutes.

2. The method of claim 1 wherein the broth or homogenate is from yeast or prokaryotes.

3. The method of claim 1 wherein the broth or homogenate is from bacteria.

4. The method of claim 1 wherein the broth or homogenate is from eubacteria.

5. The method of claim 1 wherein the broth or homogenate is from gram-negative bacteria.

6. The method of claim 1 wherein the broth or homogenate is from *E. coli*.

7. The method of claim 1 wherein the polypeptide is separated from homogenate.

8. The method of claim 1 wherein the polypeptide has a higher pI than the average pI of host proteins contained in the host cell impurities.

9. The method of claim 1 wherein the polypeptide has a pI of at least about 7.

10. The method of claim 1 wherein the polypeptide is a recombinant polypeptide.

11. The method of claim 1 wherein the polypeptide is an antibody.

12. The method of claim 1 wherein the polypeptide is a humanized antibody.

13. The method of claim 1 wherein the polypeptide is a full-length antibody.

14. The method of claim 1 wherein the polypeptide is an antibody fragment.

15. The method of claim 14 wherein the polypeptide is an antibody fragment comprising a light chain.

16. The method of claim 15 wherein the polypeptide is an antibody fragment comprising a kappa light chain.

17. The method of claim 14 wherein the polypeptide is a Fab, Fab', F(ab')$_2$, or F(ab')$_2$-leucine zipper fusion.

18. The method of claim 14 wherein the polypeptide is F(ab')$_2$.

19. The method of claim 1 wherein the polypeptide is an anti-IgE, anti-CD 18, anti-VEGF, anti-tissue factor, 2C4, anti-Her-2, anti-CD20, anti-CD40, or anti-CD11a antibody or antibody fragment.

20. The method of claim 1 wherein the polypeptide is anti-CD18 F(ab')$_2$, anti-tissue factor F(ab')$_2$, full-length anti-tissue factor antibody, or anti-VEGF antibody.

21. The method of claim 1 wherein the concentration of ethacridine lactate is about 0.1–5% weight/volume.

22. The method of claim 1 wherein the concentration of the ethacridine lactate is about 0.4–5% weight/volume.

23. The method of claim 1 wherein the concentration of the ethacridine lactate is about 0.6–5% weight/volume.

24. The method of claim 1 wherein the conductivity of the broth or homogenate after addition of the ethacridine lactate is about 1–15 mS/cm.

25. The method of claim 1 wherein the pH of the broth or homogenate after addition of the ethacridine lactate is about 5–9.

26. The method of claim 1 wherein the pH of the broth or homogenate after addition of the ethacridine lactate is about 6–9.

27. The method of claim 1 wherein the separation is accomplished by centrifugation or filtration.

28. The method of claim 1 wherein after the polypeptide is separated from the broth or homogenate, it is further purified by subjection to chromatography or filtration.

29. The method of claim 1 wherein the polypeptide is produced in a soluble fraction prior to addition of the ethyacridine lactate.

30. The method of claim 1 wherein the polypeptide is insoluble and is dissolved by contacting it with a solubilizing agent prior to addition of the ethacridine lactate.

* * * * *

SEQUENCE LISTING

```
<160> NUMBER OF SEQ ID NOS: 6

<210> SEQ ID NO 1
<211> LENGTH: 2700
<212> TYPE: DNA
<213> ORGANISM: Artificial sequence
<220> FEATURE:
<223> OTHER INFORMATION: Sequence is synthesized

<400> SEQUENCE: 1
gaattcaact tctccatact ttggataagg aaatacagac atgaaaaatc        50
tcattgctga gttgttattt aagcttgccc aaaaagaaga agagtcgaat       100
gaactgtgtg cgcaggtaga agctttggag attatcgtca ctgcaatgct       150
tcgcaatatg gcgcaaaatg accaacagcg gttgattgat caggtagagg       200
gggcgctgta cgaggtaaag cccgatgcca gcattcctga cgacgatacg       250
gagctgctgc gcgattacgt aaagaagtta ttgaagcatc ctcgtcagta       300
aaaagttaat cttttcaaca gctgtcataa agttgtcacg gccgagactt       350
atagtcgctt tgtttttatt ttttaatgta tttgtaacta gtacgcaagt       400
tcacgtaaaa agggtatcta gaattatgaa aaagaatatc gcatttcttc       450
ttgcatctat gttcgttttt tctattgcta caaacgcgta cgctgatatc       500
```

-continued

| | |
|---|---|
| cagatgaccc agtccccgag ctccctgtcc gcctctgtgg gcgatagggt | 550 |
| caccatcacc tgtcgtgcca gtcaggacat caacaattat ctgaactggt | 600 |
| atcaacagaa accaggaaaa gctccgaaac tactgattta ctatacctcc | 650 |
| accctccact ctggagtccc ttctcgcttc tctggttctg gttctgggac | 700 |
| ggattacact ctgaccatca gcagtctgca accggaggac ttcgcaactt | 750 |
| attactgtca gcaaggtaat actctgccgc cgacgttcgg acagggcacg | 800 |
| aaggtggaga tcaaacgaac tgtggctgca ccatctgtct tcatcttccc | 850 |
| gccatctgat gagcagttga aatctggaac tgcctctgtt gtgtgcctgc | 900 |
| tgaataactt ctatcccaga gaggccaaag tacagtggaa ggtggataac | 950 |
| gccctccaat cgggtaactc ccaggagagt gtcacagagc aggacagcaa | 1000 |
| ggacagcacc tacagcctca gcagcaccct gacgctgagc aaagcagact | 1050 |
| acgagaaaca caaagtctac gcctgcgaag tcacccatca gggcctgagc | 1100 |
| tcgcccgtca caaagagctt caacagggga gagtgttaat taaatcctct | 1150 |
| acgccggacg catcgtggcg agctcggtac ccggggatct aggcctaacg | 1200 |
| ctcggttgcc gccggcgttt tttattgtt gccgacgcgc atctcgactg | 1250 |
| cacggtgcac caatgcttct ggcgtcaggc agccatcgga agctgtggta | 1300 |
| tggctgtgca ggtcgtaaat cactgcataa ttcgtgtcgc tcaaggcgca | 1350 |
| ctcccgttct ggataatgtt ttttgcgccg acatcataac ggttctggca | 1400 |
| aatattctga aatgagctgt tgacaattaa tcatcgaact agtttaatgt | 1450 |
| gtggaattgt gagcggataa caattaagct taggatctag aattatgaag | 1500 |
| aagaatattg cgttcctact tgcctctatg tttgtctttt ctatagctac | 1550 |
| aaacgcgtac gctgaggttc agctggtgga gtctggcggt ggcctggtgc | 1600 |
| agccaggggg ctcactccgt ttgtcctgtg caacttctgg ctacacctt | 1650 |
| accgaataca ctatgcactg gatgcgtcag gccccgggta agggcctgga | 1700 |
| atgggttgca gggattaatc ctaaaaacgg tggtaccagc acaaccaga | 1750 |
| ggttcatgga ccgtttcact ataagcgtag ataaatccac cagtacagcc | 1800 |
| tacatgcaaa tgaacagcct gcgtgctgag gacactgccg tctattattg | 1850 |
| tgctagatgg cgaggcctga actacggctt tgacgtccgt tattttgacg | 1900 |
| tctggggtca aggaaccctg gtcaccgtct cctcggcctc caccaagggc | 1950 |
| ccatcggtct tccccctggc accctcctcc aagagcacct ctgggggcac | 2000 |
| agcggccctg ggctgcctgg tcaaggacta cttccccgaa ccggtgacgg | 2050 |
| tgtcgtggaa ctcaggcgcc ctgaccagcg gcgtgcacac cttcccggct | 2100 |
| gtcctacagt cctcaggact ctactccctc agcagcgtgg tgaccgtgcc | 2150 |
| ctccagcagc ttgggcaccc agacctacat ctgcaacgtg aatcacaagc | 2200 |
| ccagcaacac caaggtcgac aagaaagttg agcccaaatc ttgtgacaaa | 2250 |
| actcacacat gcccgccgtg cccagcacca gaactgctgg gcggccgcat | 2300 |
| gaaacagcta gaggacaagg tcgaagagct actctccaag aactaccacc | 2350 |
| tagagaatga agtggcaaga ctcaaaaaagc ttgtcgggga cgctaagca | 2400 |
| tgcgacggcc ctagagtccc taacgctcgg ttgccgccgg gcgttttta | 2450 |

```
ttgttaactc atgtttgaca gcttatcatc gataagcttt aatgcggtag         2500
tttatcacag ttaaattgct aacgcagtca ggcaccgtgt atgaaatcta         2550
acaatgcgct catcgtcatc ctcggcaccg tcaccctgga tgctgtaggc         2600
ataggcttgg ttatgccggt actgccgggc ctcttgcggg atatcgtcca         2650
ttccgacagc atcgccagtc actatggcgt gctgctagcg ctatatgcgt         2700
```

<210> SEQ ID NO 2
<211> LENGTH: 237
<212> TYPE: PRT
<213> ORGANISM: Artificial sequence
<220> FEATURE:
<223> OTHER INFORMATION: Sequence is synthesized

<400> SEQUENCE: 2

```
Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
            20                  25                  30

Pro Ser Ser Leu Ser Ala Ser Val Gly Asp Arg Val Thr Ile Thr
        35                  40                  45

Cys Arg Ala Ser Gln Asp Ile Asn Asn Tyr Leu Asn Trp Tyr Gln
    50                  55                  60

Gln Lys Pro Gly Lys Ala Pro Lys Leu Leu Ile Tyr Tyr Thr Ser
65                  70                  75

Thr Leu His Ser Gly Val Pro Ser Arg Phe Ser Gly Ser Gly Ser
                80                  85                  90

Gly Thr Asp Tyr Thr Leu Thr Ile Ser Ser Leu Gln Pro Glu Asp
            95                 100                 105

Phe Ala Thr Tyr Tyr Cys Gln Gln Gly Asn Thr Leu Pro Pro Thr
        110                 115                 120

Phe Gly Gln Gly Thr Lys Val Glu Ile Lys Arg Thr Val Ala Ala
    125                 130                 135

Pro Ser Val Phe Ile Phe Pro Pro Ser Asp Glu Gln Leu Lys Ser
140                 145                 150

Gly Thr Ala Ser Val Val Cys Leu Leu Asn Asn Phe Tyr Pro Arg
                155                 160                 165

Glu Ala Lys Val Gln Trp Lys Val Asp Asn Ala Leu Gln Ser Gly
            170                 175                 180

Asn Ser Gln Glu Ser Val Thr Glu Gln Asp Ser Lys Asp Ser Thr
        185                 190                 195

Tyr Ser Leu Ser Ser Thr Leu Thr Leu Ser Lys Ala Asp Tyr Glu
    200                 205                 210

Lys His Lys Val Tyr Ala Cys Glu Val Thr His Gln Gly Leu Ser
215                 220                 225

Ser Pro Val Thr Lys Ser Phe Asn Arg Gly Glu Cys
                230                 235
```

<210> SEQ ID NO 3
<211> LENGTH: 300
<212> TYPE: PRT
<213> ORGANISM: Artificial sequence
<220> FEATURE:
<223> OTHER INFORMATION: Sequence is synthesized

<400> SEQUENCE: 3

Met Lys Lys Asn Ile Ala Phe Leu Leu Ala Ser Met Phe Val Phe

```
              1               5              10              15
Ser Ile Ala Thr Asn Ala Tyr Ala Glu Val Gln Leu Val Glu Ser
                 20                  25                  30
Gly Gly Gly Leu Val Gln Pro Gly Gly Ser Leu Arg Leu Ser Cys
                 35                  40                  45
Ala Thr Ser Gly Tyr Thr Phe Thr Glu Tyr Thr Met His Trp Met
                 50                  55                  60
Arg Gln Ala Pro Gly Lys Gly Leu Glu Trp Val Ala Gly Ile Asn
                 65                  70                  75
Pro Lys Asn Gly Gly Thr Ser His Asn Gln Arg Phe Met Asp Arg
                 80                  85                  90
Phe Thr Ile Ser Val Asp Lys Ser Thr Ser Thr Ala Tyr Met Gln
                 95                 100                 105
Met Asn Ser Leu Arg Ala Glu Asp Thr Ala Val Tyr Tyr Cys Ala
                110                 115                 120
Arg Trp Arg Gly Leu Asn Tyr Gly Phe Asp Val Arg Tyr Phe Asp
                125                 130                 135
Val Trp Gly Gln Gly Thr Leu Val Thr Val Ser Ser Ala Ser Thr
                140                 145                 150
Lys Gly Pro Ser Val Phe Pro Leu Ala Pro Ser Ser Lys Ser Thr
                155                 160                 165
Ser Gly Gly Thr Ala Ala Leu Gly Cys Leu Val Lys Asp Tyr Phe
                170                 175                 180
Pro Glu Pro Val Thr Val Ser Trp Asn Ser Gly Ala Leu Thr Ser
                185                 190                 195
Gly Val His Thr Phe Pro Ala Val Leu Gln Ser Ser Gly Leu Tyr
                200                 205                 210
Ser Leu Ser Ser Val Val Thr Val Pro Ser Ser Ser Leu Gly Thr
                215                 220                 225
Gln Thr Tyr Ile Cys Asn Val Asn His Lys Pro Ser Asn Thr Lys
                230                 235                 240
Val Asp Lys Lys Val Glu Pro Lys Ser Cys Asp Lys Thr His Thr
                245                 250                 255
Cys Pro Pro Cys Pro Ala Pro Glu Leu Leu Gly Gly Arg Met Lys
                260                 265                 270
Gln Leu Glu Asp Lys Val Glu Glu Leu Leu Ser Lys Asn Tyr His
                275                 280                 285
Leu Glu Asn Glu Val Ala Arg Leu Lys Lys Leu Val Gly Glu Arg
                290                 295                 300

<210> SEQ ID NO 4
<211> LENGTH: 3100
<212> TYPE: DNA
<213> ORGANISM: Artificial sequence
<220> FEATURE:
<223> OTHER INFORMATION: Sequence is synthesized

<400> SEQUENCE: 4
gaattcaact tctccatact ttggataagg aaatacagac atgaaaaatc          50
tcattgctga gttgttattt aagcttgccc aaaaagaaga agagtcgaat         100
gaactgtgtg cgcaggtaga agctttggag attatcgtca ctgcaatgct         150
tcgcaatatg gcgcaaaatg accaacagcg gttgattgat caggtagagg         200
gggcgctgta cgaggtaaag cccgatgcca gcattcctga cgacgatacg         250
```

-continued

| | |
|---|---|
| gagctgctgc gcgattacgt aaagaagtta ttgaagcatc ctcgtcagta | 300 |
| aaaagttaat cttttcaaca gctgtcataa agttgtcacg gccgagactt | 350 |
| atagtcgctt tgttttcatt ttttaatgta tttgtaacta gtacgcaagt | 400 |
| tcacgtaaaa agggtatcta gaattatgaa aaagaatatc gcatttcttc | 450 |
| ttgcatctat gttcgttttt tctattgcta caaacgcgta cgctgatatc | 500 |
| cagatgaccc agtccccgag ctccctgtcc gcctctgtgg gcgataggggt | 550 |
| caccatcacc tgcagagcca gtcgcgacat caagagctat ctgaactggt | 600 |
| atcaacagaa accaggaaaa gctccgaaag tactgattta ctatgctact | 650 |
| agtctcgctg aaggagtccc ttctcgcttc tctggatccg gttctgggac | 700 |
| ggattacact ctgaccatca gcagtctgca gccagaagac ttcgcaactt | 750 |
| attactgtct tcagcacgga gagtctccat ggacatttgg acagggtacc | 800 |
| aaggtggaga tcaaacgaac tgtggctgca ccatctgtct tcatcttccc | 850 |
| gccatctgat gagcagttga aatctggaac tgcttctgtt gtgtgcctgc | 900 |
| tgaataactt ctatcccaga gaggccaaag tacagtggaa ggtggataac | 950 |
| gccctccaat cgggtaactc ccaggagagt gtcacagagc aggacagcaa | 1000 |
| ggacagcacc tacagcctca gcagcaccct gacgctgagc aaagcagact | 1050 |
| acgagaaaca caaagtctac gcctgcgaag tcacccatca gggcctgagc | 1100 |
| tcgcccgtca caaagagctt caacagggga gagtgttaat taaatcctct | 1150 |
| acgccggacg catcgtggcg agctcggtac ccggggatct aggcctaacg | 1200 |
| ctcggttgcc gccgggcgtt ttttattgtt gccgacgcgc atctcgactg | 1250 |
| cacggtgcac caatgcttct ggcgtcaggc agccatcgga agctgtggta | 1300 |
| tggctgtgca ggtcgtaaat cactgcataa ttcgtgtcgc tcaaggcgca | 1350 |
| ctcccgttct ggataatgtt ttttgcgccg acatcataac ggttctggca | 1400 |
| aatattctga aatgagctgt tgacaattaa tcatcgaact agtttaatgt | 1450 |
| gtggaattgt gagcggataa caattaagct taggatctag aattatgaag | 1500 |
| aagaatattg cgttcctact tgcctctatg tttgtctttt ctatagctac | 1550 |
| aaacgcgtac gctgaggttc agctggtgga gtctggcggt ggcctggtgc | 1600 |
| agccagggggg ctcactccgt ttgtcctgtg cagcttctgg cttcaatatt | 1650 |
| aaggagtact acatgcactg ggtccgtcag gccccgggta agggcctgga | 1700 |
| atgggttgga ttgattgatc cagagcaagg caacacgatc tatgacccga | 1750 |
| agttccagga ccgtgccact ataagcgctg acaattccaa aaacacagca | 1800 |
| tacctgcaga tgaacagcct gcgtgctgag gacactgccg tctattattg | 1850 |
| tgctcgagac acgccgcctt acttcgacta ctggggtcaa ggaaccctgg | 1900 |
| tcaccgtctc ctcggcctcc accaagggcc catcggtctt ccccctggca | 1950 |
| ccctcctcca agagcacctc tgggggcaca gcggccctgg gctgcctggt | 2000 |
| caaggactac ttccccgaac cggtgacggt gtcgtggaac tcaggcgccc | 2050 |
| tgaccagcgg cgtgcacacc ttcccggctg tcctacagtc ctcaggactc | 2100 |
| tactccctca gcagcgtggt gactgtgccc tctagcagct gggcaccca | 2150 |
| gacctacatc tgcaacgtga atcacaagcc cagcaacacc aaggtggaca | 2200 |
| agaaagttga gcccaaatct tgtgacaaaa ctcacacatg cccaccgtgc | 2250 |

-continued

```
ccagcacctg aactcctggg gggaccgtca gtcttcctct tccccccaaa         2300
acccaaggac accctcatga tctcccggac ccctgaggtc acatgcgtgg         2350
tggtggacgt gagccacgaa gaccctgagg tcaagttcaa ctggtacgtg         2400
gacggcgtgg aggtgcataa tgccaagaca aagccgcggg aggagcagta         2450
caacagcacg taccgtgtgg tcagcgtcct caccgtcctg caccaggact         2500
ggctgaatgg caaggagtac aagtgcaagg tctccaacaa agccctccca         2550 gccccatcg agaaaaccat ctccaaagcc aaagggcagc cccgagaacc          2600
acaggtgtac accctgcccc catcccggga agagatgacc aagaaccagg         2650
tcagcctgac ctgcctggtc aaaggcttct atcccagcga catcgccgtg         2700
gagtgggaga gcaatgggca gccggagaac aactacaaga ccacgcctcc         2750
cgtgctggac tccgacggct ccttcttcct ctacagcaag ctcaccgtgg         2800
acaagagcag gtggcagcag gggaacgtct tctcatgctc cgtgatgcat         2850
gaggctctgc acaaccacta cacgcagaag agcctctccc tgtctccggg         2900
taaataagca tgcgacggcc ctagagtccc taacgctcgg ttgccgccgg         2950 gcgttttttta ttgttaactc atgtttgaca gcttatcatc gataagcttt        3000
aatgcggtag tttatcacag ttaaattgct aacgcagtca ggcaccgtgt         3050
atgaaatcta acaatgcgct catcgtcatc ctcggcaccg tcaccctgga         3100
```

<210> SEQ ID NO 5
<211> LENGTH: 237
<212> TYPE: PRT
<213> ORGANISM: Artificial sequence
<220> FEATURE:
<223> OTHER INFORMATION: Sequence is synthesized

<400> SEQUENCE: 5

```
Met Lys Lys Asn Ile Ala Phe Leu Leu Ala Ser Met Phe Val Phe
  1               5                  10                  15

Ser Ile Ala Thr Asn Ala Tyr Ala Asp Ile Gln Met Thr Gln Ser
                 20                  25                  30

Pro Ser Ser Leu Ser Ala Ser Val Gly Asp Arg Val Thr Ile Thr
                 35                  40                  45

Cys Arg Ala Ser Arg Asp Ile Lys Ser Tyr Leu Asn Trp Tyr Gln
                 50                  55                  60

Gln Lys Pro Gly Lys Ala Pro Lys Val Leu Ile Tyr Tyr Ala Thr
                 65                  70                  75

Ser Leu Ala Glu Gly Val Pro Ser Arg Phe Ser Gly Ser Gly Ser
                 80                  85                  90

Gly Thr Asp Tyr Thr Leu Thr Ile Ser Ser Leu Gln Pro Glu Asp
                 95                 100                 105

Phe Ala Thr Tyr Tyr Cys Leu Gln His Gly Glu Ser Pro Trp Thr
                110                 115                 120

Phe Gly Gln Gly Thr Lys Val Glu Ile Lys Arg Thr Val Ala Ala
                125                 130                 135

Pro Ser Val Phe Ile Phe Pro Pro Ser Asp Glu Gln Leu Lys Ser
                140                 145                 150

Gly Thr Ala Ser Val Val Cys Leu Leu Asn Asn Phe Tyr Pro Arg
                155                 160                 165

Glu Ala Lys Val Gln Trp Lys Val Asp Asn Ala Leu Gln Ser Gly
```

-continued

```
                        170                 175                 180
Asn Ser Gln Glu Ser Val Thr Glu Gln Asp Ser Lys Asp Ser Thr
                    185                 190                 195
Tyr Ser Leu Ser Ser Thr Leu Thr Leu Ser Lys Ala Asp Tyr Glu
                200                 205                 210
Lys His Lys Val Tyr Ala Cys Glu Val Thr His Gln Gly Leu Ser
            215                 220                 225
Ser Pro Val Thr Lys Ser Phe Asn Arg Gly Glu Cys
        230                 235

<210> SEQ ID NO 6
<211> LENGTH: 470
<212> TYPE: PRT
<213> ORGANISM: Artificial sequence
<220> FEATURE:
<223> OTHER INFORMATION: Sequence is synthesized

<400> SEQUENCE: 6

Met Lys Lys Asn Ile Ala Phe Leu Leu Ala Ser Met Phe Val Phe
  1               5                  10                  15
Ser Ile Ala Thr Asn Ala Tyr Ala Glu Val Gln Leu Val Glu Ser
                 20                  25                  30
Gly Gly Gly Leu Val Gln Pro Gly Gly Ser Leu Arg Leu Ser Cys
             35                  40                  45
Ala Ala Ser Gly Phe Asn Ile Lys Glu Tyr Tyr Met His Trp Val
         50                  55                  60
Arg Gln Ala Pro Gly Lys Gly Leu Glu Trp Val Gly Leu Ile Asp
     65                  70                  75
Pro Glu Gln Gly Asn Thr Ile Tyr Asp Pro Lys Phe Gln Asp Arg
 80                  85                  90
Ala Thr Ile Ser Ala Asp Asn Ser Lys Asn Thr Ala Tyr Leu Gln
             95                 100                 105
Met Asn Ser Leu Arg Ala Glu Asp Thr Ala Val Tyr Tyr Cys Ala
            110                 115                 120
Arg Asp Thr Ala Ala Tyr Phe Asp Tyr Trp Gly Gln Gly Thr Leu
            125                 130                 135
Val Thr Val Ser Ser Ala Ser Thr Lys Gly Pro Ser Val Phe Pro
            140                 145                 150
Leu Ala Pro Ser Ser Lys Ser Thr Ser Gly Gly Thr Ala Ala Leu
            155                 160                 165
Gly Cys Leu Val Lys Asp Tyr Phe Pro Glu Pro Val Thr Val Ser
            170                 175                 180
Trp Asn Ser Gly Ala Leu Thr Ser Gly Val His Thr Phe Pro Ala
            185                 190                 195
Val Leu Gln Ser Ser Gly Leu Tyr Ser Leu Ser Ser Val Val Thr
            200                 205                 210
Val Pro Ser Ser Ser Leu Gly Thr Gln Thr Tyr Ile Cys Asn Val
            215                 220                 225
Asn His Lys Pro Ser Asn Thr Lys Val Asp Lys Lys Val Glu Pro
            230                 235                 240
Lys Ser Cys Asp Lys Thr His Thr Cys Pro Pro Cys Pro Ala Pro
            245                 250                 255
Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val
```

```
                     275                 280                 285
Val Val Asp Val Ser His Glu Asp Pro Glu Val Lys Phe Asn Trp
                290                 295                 300
Tyr Val Asp Gly Val Glu Val His Asn Ala Lys Thr Lys Pro Arg
                305                 310                 315
Glu Glu Gln Tyr Asn Ser Thr Tyr Arg Val Val Ser Val Leu Thr
                320                 325                 330
Val Leu His Gln Asp Trp Leu Asn Gly Lys Glu Tyr Lys Cys Lys
                335                 340                 345
Val Ser Asn Lys Ala Leu Pro Ala Pro Ile Glu Lys Thr Ile Ser
                350                 355                 360
Lys Ala Lys Gly Gln Pro Arg Glu Pro Gln Val Tyr Thr Leu Pro
                365                 370                 375
Pro Ser Arg Glu Glu Met Thr Lys Asn Gln Val Ser Leu Thr Cys
                380                 385                 390
Leu Val Lys Gly Phe Tyr Pro Ser Asp Ile Ala Val Glu Trp Glu
                395                 400                 405
Ser Asn Gly Gln Pro Glu Asn Asn Tyr Lys Thr Thr Pro Pro Val
                410                 415                 420
Leu Asp Ser Asp Gly Ser Phe Phe Leu Tyr Ser Lys Leu Thr Val
                425                 430                 435
Asp Lys Ser Arg Trp Gln Gln Gly Asn Val Phe Ser Cys Ser Val
                440                 445                 450
Met His Glu Ala Leu His Asn His Tyr Thr Gln Lys Ser Leu Ser
                455                 460                 465
Leu Ser Pro Gly Lys
                470
```